United States Patent
Bemis et al.

(10) Patent No.: US 6,849,267 B2
(45) Date of Patent: Feb. 1, 2005

(54) COMPOSITIONS USEFUL AS INHIBITORS OF ERK

(75) Inventors: Guy Bemis, Arlington, MA (US); Xiaoling Xie, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 348 days.

(21) Appl. No.: 09/971,533

(22) Filed: Oct. 5, 2001

(65) Prior Publication Data

US 2003/0049820 A1 Mar. 13, 2003

Related U.S. Application Data

(63) Continuation of application No. PCT/US01/03904, filed on Feb. 5, 2001.
(60) Provisional application No. 60/180,502, filed on Feb. 5, 2000, and provisional application No. 60/191,959, filed on Mar. 24, 2000.

(51) Int. Cl.$^7$ .............................. A61F 2/02; A61F 6/06; A61F 13/02; A61L 9/04; A61K 9/70
(52) U.S. Cl. ....................... 424/423; 424/430; 424/434; 424/435; 424/443; 424/45
(58) Field of Search ................................ 424/423, 430, 424/434, 435, 443, 45

(56) References Cited

FOREIGN PATENT DOCUMENTS

WO      WO9910325 A1 *    3/1999

* cited by examiner

*Primary Examiner*—Carlos A. Azpuru
(74) *Attorney, Agent, or Firm*—Andrea Robidoux Vertex Pharmaceuticals Incorporated

(57) ABSTRACT

This invention provides a method of treating a disease state in mammals that is alleviated by treatment with a protein kinase inhibitor, especially an ERK inhibitor, which method comprises administering a compound having the pharmacophoric features Grp1, Grp2 and Grp3:

Grp 1 is an optionally substituted aryl or aliphatic group; Grp 2 is a heteroaromatic ring having one to three nitrogens, said ring comprising a hydrogen bond acceptor HBA2 optionally bonded to a hydrogen bond donor HBD2, and Grp3 is a heteroaromatic ring comprising a hydrogen bond donor HBD1, with distances between the pharmacophoric features defined in the specification. The method is useful for treating cancer, stroke, diabetes, hepatomegaly, cardiovascular disease, Alzheimer's disease, cystic fibrosis, viral disease, autoimmune diseases, atherosclerosis, restenosis, psoriasis, allergic reactions, inflammation, neurological disorders or a hormone-related disease.

11 Claims, No Drawings

COMPOSITIONS USEFUL AS INHIBITORS OF ERK

This application continuation of co-pending International Patent Application PCT/US01/03904, filed Feb. 5, 2001, which claims priority of U.S. Provisional Application Ser. No. 60/180,502 filed Feb. 5, 2000 and U.S. Provisional Application Ser. No. 60/191,959 filed Mar. 24, 2000. The entirety of which is herein incorporated by reference.

FIELD OF THE INVENTION

The present invention is in the field of medicinal chemistry and relates to compounds that are protein kinase inhibitors, compositions containing such compounds and methods of use. More particularly, the compounds are inhibitors of ERK and are useful for treating disease states, such as cancer, that are alleviated by ERK inhibitors.

BACKGROUND OF THE INVENTION

Mammalian mitogen-activated protein (MAP)1 kinases are serine/threonine kinases that mediate intracellular signal transduction pathways (Cobb and Goldsmith, 1995, *J Biol. Chem.* 270, 14843; Davis, 1995, *Mol. Reprod. Dev.* 42, 459). Members of the MAP kinase family share sequence similarity and conserved structural domains, and include the ERK (extracellular signal regulated kinase), JNK (Jun N-terminal kinase) and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995,*J Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996,*Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995,*J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997,*Am. J. Respir. Cell Mol. Biol.* 16, 589).

Based on these findings, ERK signalling has been implicated various disease states including, but not limited to, cancer, inflammation, cardiovascular disease, and neurological disorders, among others.

There is a high unmet medical need to develop protein kinase inhibitors, especially ERK inhibitors, that are useful in treating the various conditions associated with ERK activation, especially considering the currently available, relatively inadequate treatment options for the majority of these conditions.

Accordingly, there is still a great need to develop potent inhibitors of protein kinase, including ERK inhibitors, that are useful in treating various conditions associated with ERK activation.

DESCRIPTION OF THE INVENTION

It has now been discovered that compounds possessing certain pharmacophoric features as described below are inhibitors of protein kinase, particularly inhibitors of ERK enzyme. The compounds are useful in a method for treating a disease state in mammals that is alleviated by treatment with a protein kinase inhibitor. The method comprises administering to a patient in need of such a treatment a therapeutically effective amount of a compound comprising Grp1, Grp2, and Grp3:

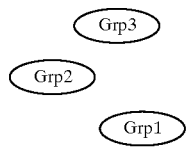

wherein:
  Grp 1 is an optionally substituted aryl or aliphatic group;
  Grp 2 is a heteroaromatic ring comprising one to three nitrogens, and a hydrogen bond acceptor HBA2, wherein HBA2 is optionally bonded to a hydrogen bond donor HBD2; and
  Grp3 is a heteroaromatic ring comprising a hydrogen bond donor HBD1; wherein
  said compound optionally comprises a hydrogen bond acceptor HBA1; and wherein
  Grp1 is within about 2.5–10.0 Å of Grp2; Grp2 is within about 4.0–8.0 Å of Grp3; Grp3 is within about 5.0–12.0 Å of Grp1; HBA2 is within about 6.5–11.0 Å of Grp1; HBD1 is within about 6.5–8.5 Å of Grp2; HBD1 is within about 3.5–5.5 Å of HBA1; and HBA1 is within about 6.7–14.0 Å of HBD2.

As used herein, the following definitions shall apply unless otherwise indicated. The term "aliphatic" as used herein means straight chained, branched or cyclic $C_1$–$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O or S and shall include any oxidized form of nitrogen and sulfur, and the quaternized form of any basic nitrogen.

The term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, or 3-thienyl. The term "aryl ring" also refers to rings that are optionally substituted.

Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclic ring, for example, indanyl or tetrahydrobenzopyranyl.

Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-1-alkyl-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane. The term "heterocyclic ring", whether saturated or unsaturated, also refers to rings that are optionally substituted.

An aryl group (carbocyclic and heterocyclic) or an aralkyl group, such as benzyl or phenethyl, may contain one or more substituents. Examples of suitable substituents on the unsaturated carbon atom of an aryl group include a halogen, —R, —OR, —OH, —SH, —SR, protected OH (such as acyloxy), phenyl (Ph), substituted Ph, —OPh, substituted —OPh, —NO$_2$, —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, or —NHS(O)$_2$R, where R is an aliphatic group or a substituted aliphatic group.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon as well as the following: =O, =S, =NNHR, =NNR$_2$, =N—OR, =NNHCOR, =NNHCO$_2$R, =NNHSO$_2$R, or =NR.

The term "alkylidene chain" refers to an optionally substituted, straight or branched, carbon chain that may be fully saturated or have one or more units of unsaturation. The optional substituents are as described above for an aliphatic group.

A substitutable nitrogen on an aromatic or non-aromatic heterocyclic ring may be optionally substituted. Suitable substituents on the nitrogen include R, COR, S(O)$_2$R, and CO$_2$R, where R is an aliphatic group or a substituted aliphatic group.

The term "linker group" means an organic moiety that connects two parts of a compound. Linkers are typically comprised of an atom such as oxygen or sulfur, a unit such as —NH— or —CH$_2$—, or a chain of atoms, such as an alkylidene chain. The molecular mass of a linker is typically in the range of about 14 to 200. Examples of linkers include a saturated or unsaturated C$_{1-6}$ alkylidene chain which is optionally substituted, and wherein up to two saturated carbons of the chain are optionally replaced by —C(=O)—, —CONH—, CONHNH—, —CO$_2$—, —NHCO$_2$—, —O—, —NHCONH—, —OC(=O)—, —OC(=O)NH—, —NHNH—, —NHCO—, —O—, —S—, —SO—, —SO$_2$—, —NH—, —SO$_2$NH—, or NHSO$_2$—.

The terms "backbone chain" and "backbone" refer to the portion of a polypeptide which comprises the repeating unit —CO—CH—NH—.

The term "substitute" refers to the replacement of a hydrogen atom in a compound with a substituent group. The term "substitute" does not include those hydrogen atoms which form a part of a hydrogen bonding moiety which is capable of forming a hydrogen bond with a suitable hydrogen bond acceptor, such as a carbonyl oxygen, of an amino acid residue in the kinase binding site.

The term "strain energy" is used in this application to refer to the difference between the conformational energy of the unbound (or free) compound and that of the compound when bound to kinase. The strain energy can be determined by the following steps: Evaluate the energy of the molecule when it has the conformation necessary for binding to kinase. Then minimize and reevaluate the energy—this is the strain energy. A more comprehensive definition of strain energy can be found in Bostrom, J., Norrby, P.-O.; Liljefors, T., "Conformational Energy Penalties of Protein-Bound Ligands", *J. Comput. Aided Mol. Design*, 1998, 383. The strain energy for binding of a potential inhibitor to kinase is the difference between the free conformation energy and the bound conformation energy. In a preferred embodiment, the strain energy of an inhibitor of the present invention is less than about 10 kcal/mol.

The term "hydrophobic" refers to a moiety which tends not to dissolve in water and is fat-soluble. Hydrophobic moieties include, but are not limited to, hydrocarbons, such as alkanes, alkenes, alkynes, cycloalkanes, cycloalkenes, cycloalkynes and aromatic compounds, such as aryls, certain saturated and unsaturated heterocycles and moieties that are substantially similar to the side chains of hydrophobic natural and unnatural α-amino acids, including valine, leucine, isoleucine, methionine, phenylanine, α-amino isobutyric acid, alloisoleucine, tyrosine, and tryptophan.

The term "moderately hydrophobic" refers to a hydrophobic moiety in which one or two carbon atoms have been replaced with one or more polar atoms, such as oxygen or nitrogen.

The term "hydrogen bond" refers to a favorable interaction that occurs whenever a suitable donor atom, X, bearing a proton, H, and a suitable acceptor atom, Y, have a separation of between 2.5 Å and 3.5 Å and where the angle X-H - - - Y is greater than 90 degrees. Suitable donor and acceptor atoms are well understood in medicinal chemistry (G. C. Pimentel and A. L. McClellan, *The Hydrogen Bond*, Freeman, San Francisco, 1960; R. Taylor and O. Kennard, "Hydrogen Bond Geometry in Organic Crystals", *Accounts of Chemical Research*, 17, pp. 320–326 (1984)).

The compounds of this invention were designed to bind to protein kinase, particularly ERK, at the ATP binding site of the enzyme. The structure of this binding site has been described for rat ERK2 (Boulton T. G. et al., 1991, *Cell* 65, 663) and for human ERK2 Owaki H. et al., 1992, *Biochem. Biophys. Res. Commun.*, 182, 1416). The accession number for the human ERK2 protein structure in the Swiss-Prot database is P28482.

The practitioner skilled in the art will appreciate that there are a number of means to design the inhibitors of the present invention. These same means may be used to select a candidate compound for screening as an ERK inhibitor. This design or selection may begin with selection of the various moieties which fill binding pockets.

There are a number of ways to select moieties to fill individual binding pockets. These include visual inspection of a physical model or computer model of the active site and manual docking of models of selected moieties into various binding pockets. Modeling software that is well known and available in the art may be used. These include QUANTA [Molecular Simulations, Inc., Burlington, Mass., 1992], SYBYL [Molecular Modeling Software, Tripos Associates, Inc., St. Louis, Mo., 1992]. This modeling step may be followed by energy minimization with standard molecular mechanics forcefields such as CHARMM and AMBER. [AMBER: (S. J. Weiner, P. A. Kollman, D. A. Case, U. C. Singh, C. Ghio, G. Alagona, and P. Weiner, *J. Am. Chem. Soc.*, 1984, 106, 765); CHARMM: (B. R. Brooks, R. E. Bruccoleri, B. D. Olafson, D. J. States, S Swaminathan, and M. Karplus, *J. Comp. Chem.* 1983, 4, 187). In addition, there are a number of more specialized computer programs to assist in the process of optimally placing either complete molecules or molecular fragments into the protein binding site. These include:

1. GRID (Goodford, P. J. A Computational Procedure for Determining Energetically Favorable Binding Sites on Biologically Important Macromolecules. J. Med. Chem. 1985, 28, 849–857). GRID is available from Oxford University, Oxford, UK.
2. MCSS (Miranker, A.; Karplus, M. Functionality Maps of Binding Sites: A Multiple Copy Simultaneous Search Method. Proteins: Structure, Function and Genetics 1991, 11, 29-34). MCSS is available from Molecular Simulations, Burlington, Mass.
3. DOCK (Kuntz, I. D.; Blaney, J. M.; Oatley, S. J.; Langridge, R.; Ferrin, T. E. A Geometric Approach to Macromolecule-Ligand Interactions. J. Mol. Biol. 1982, 161, 269–288). DOCK is available from the University of California, San Francisco, Calif.

Once suitable binding orientations have been selected, complete molecules can be chosen for biological evaluation. In the case of molecular fragments, they can be assembled into a single inhibitor. This assembly may be accomplished by connecting the various moieties to a central scaffold. The assembly process may, for example, be done by visual inspection followed by manual model building, again using software such as Quanta or Sybyl. A number of other programs may also be used to help select ways to connect the various moieties. These include:

1. CAVEAT (Bartlett, P. A.; Shea, G. T.; Telfer, S. J.; Waterman, S. CAVEAT: A Program to Facilitate the Structure-Derived Design of Biologically Active Molecules. In "Molecular Recognition in Chemical and Biological Problems," Special Pub., Royal Chem. Soc. 1989, 78, 182–196). CAVEAT is available from the University of California, Berkeley, Calif.
2. 3D Database systems such as MACCS-3D (MDL Information Systems, San Leandro, Calif.). This area has been recently reviewed by Martin (Martin, Y. C. 3D Database Searching in Drug Design. *J. Med. Chem.* 1992, 35, 2145).
3. HOOK (available from Molecular Simulations, Burlington, Mass.)

In addition to the above computer assisted modeling of inhibitor compounds, the inhibitors of this invention may be constructed "de novo" using either an empty active site or optionally including some portions of a known inhibitor. Such methods are well known in the art. They include, for example:

1. LUDI (Bohm, H. J. The Computer Program LUDI: A New Method for the De Novo Design of Enzyme Inhibitors. *J. Comp. Aid. Molec. Design.* 1992, 6, 61–78). LUDI is available from Biosym Technologies, San Diego, Calif.
2. LEGEND (Nishibata, Y., Itai, A., *Tetrahedron*, 1991, 47, 8985). LEGEND is available from Molecular Simultations, Burlington, Mass.
3. LeapFrog (available from Tripos Associates, St. Louis, Mo.)

A number of techniques commonly used for modeling drugs may be employed (For a review, see: Cohen, N. C.; Blaney, J. M.; Humblet, C.; Gund, P.; Barry, D. C., "Molecular Modeling Software and Methods for Medicinal Chemistry", *J. Med. Chem.*, 1990, 33, 883). There are likewise a number of examples in the chemical literature of techniques that can be applied to specific drug design projects. For a review, see: Navia, M. A. and Murcko, M. A., *Current Opinions in Structural Biology*, 1992, 2, 202. Some examples of these specific applications include: Baldwin, J. J. et al., *J. Med. Chem.*, 1989, 32, 2510; Appelt, K. et al., *J. Med. Chem.*, 1991, 34, 1925; and Ealick, S. E. et al., *Proc. Nat. Acad. Sci. USA*, 1991, 88, 11540.

Using the novel combination of steps of the present invention, the skilled artisan can advantageously reduce time consuming and expensive experimentation to determine enzymatic inhibition activity of particular compounds. The method also is useful to facilitate rational design of kinase inhibitors and therapeutic or prophylactic treatments against kinase-mediated diseases. Accordingly, the present invention relates to such inhibitors.

A variety of conventional techniques may be used to carry out each of the above evaluations as well as the evaluations necessary in screening a candidate compound for protein kinase inhibiting activity. Generally, these techniques involve determining the location and binding proximity of a given moiety, the occupied space of a bound inhibitor, the amount of complementary contact surface between the inhibitor and protein, the deformation energy of binding of a given compound and some estimate of hydrogen bonding strength and/or electrostatic interaction energies. Examples of conventional techniques useful in the above evaluations include: quantum mechanics, molecular mechanics, molecular dynamics, Monte Carlo sampling, systematic searches and distance geometry methods [G. R. Marshall, *Ann. Rev. Pharmacol. Toxicol.*, 1987, 27, 193]. Specific computer software has been developed for use in carrying out these methods. Examples of programs designed for such uses include: Gaussian 92, revision E.2 [M. J. Frisch, Gaussian, Inc., Pittsburgh, Pa. ©1993]; AMBER, version 4.0 [P. A. Kollman, University of California at San Francisco, ©1993]; QUANTA/CHARMM [Molecular Simulations, Inc., Burlington, Mass. ©1992]; and Insight II/Discover [Biosysm Technologies Inc., San Diego, Calif. ©1992]. These programs may be implemented, for instance, using a Silicon Graphics Indigo2 workstation or personal computer network. Other hardware systems and software packages will be known and of evident applicability to those skilled in the art.

Different classes of active protein kinase inhibitors, according to this invention, may interact in similar ways with the various binding regions of the protein kinase active site, particularly the ERK active site. The spatial arrangement of these important groups is often referred to as a pharmacophore. The concept of the pharmacophore has been well described in the literature [D. Mayer, C. B. Naylor, I. Motoc, and G. R. Marshall, *J. Comp. Aided Molec. Design,* 1987, 1, 3; A. Hopfinger and B. J. Burke, in *Concepts and Applications of Molecular Similarity,* 1990, M. A. Johnson and G. M. Maggiora, Ed., Wiley].

Different classes of kinase inhibitors of this invention may also use different scaffolds or core structures, but all of these cores will allow the necessary moieties to be placed in the active site such that the specific interactions necessary for binding may be obtained. These compounds are best defined in terms of their ability to match the pharmacophore, i.e., their structural identity relative to the shape and properties of the active site of the kinase enzyme such as ERK.

Distances to or from any given group are calculated from the center of mass of that group. The term "center of mass" refers to a point in three-dimensional space which represents a weighted average position of the masses that make up an object. Distances between groups may be readily determined using any pharmacophore modeling software and other suitable chemical structure software. Examples of pharmacophore modeling software that are commercially available include:

1. DISCO (Martin, Y. C., Bures, M. G., Danaher, E. A., DeLazzer, J., Lico, A., Pavlik, P. A., *J. Comput. Aided Mol. Design,* 1993, 7, 83). DISCO is available from Tripos Associates, St. Louis, Mo.
2. CHEM-X which is developed and distributed by Chemical Design Ltd, Oxon, UK and Mahwah, N.J.
3. APEX-3D which is part of the Insight molecular modeling program, distributed by Molecular Simulations, Inc., San Diego, Calif.
4. CATALYST (Sprague, P. W., *Perspectives in Drug Discovery and Design,* 1995, 3, 1; Müller, K., Ed., ESCOM, Leiden) CATALYST is distributed by Molecular Simulations, Inc., San Diego, Calif.

A typical hydrogen bond acceptor (HBA) is an oxygen or nitrogen, especially an oxygen or nitrogen that is $sp^2$-hybridized or an ether oxygen. A typical hydrogen bond donor (HBD) is an oxygen, nitrogen, or heteroaromatic carbon that bears a hydrogen. When bound to ERK, compounds of this invention bind to the ATP binding site of the enzyme. During such binding, Grp1 will occupy a region of the ATP binding site bounded (within about 5.0 Å of Grp1) by the following amino acids: Val39, Thr110, Asp111, Lys114, and Leu 156. The amino acid numbering used herein corresponds to that of the human ERK2 enzyme. This amino acid numbering corresponds to the Swiss-Prot database entry for accession #P28482. The Swiss-Prot database is an international protein sequence database distributed by the European Bioinformatics Institute (EBI) in Geneva, Switzerland. The database can be found at www.ebi.ac.uk/swissprot.

Examples of suitable Grp1 moieties include optionally substituted aliphatic groups and aryl rings. A preferred Grp1 is an optionally substituted phenyl ring.

Grp2 will occupy a region of the ATP binding site bounded (within about 5.0 Å) by the following amino acids: Val39, Ala52, Ile84, Asp106, Leu107, Met108, and Leu156. This relatively small binding pocket favors moieties that have a hydrogen bond acceptor HBA2 in a ring where the positions ortho to the hydrogen bond acceptor have a substituent no larger than a $C_1$–$C_6$ alkyl group. Preferably the positions ortho to $HBA_2$ are substituted with either hydrogen, methyl, or NHR, preferably hydrogen. Ideally, Grp2 will be capable of orienting in the binding pocket such that HBA2 can form a hydrogen bond with a backbone amino hydrogen of Met108. In this orientation, hydrogen bond donor HBD2, if present, will form a hydrogen bond with either the backbone carbonyl of Met108 or the backbone carbonyl of Asp106. Examples of suitable Grp2 moieties are listed in Table 1 below. In the examples, the exocyclic lines indicate positions where Grp2 may be attached to either Grp1 or Grp3. The distance between Grp2 and Grp1 will be in the range of about 2.5 to about 10.0 Å, preferably between about 3.9 to about 8.0 Å, and most preferably between about 5.7 and 6.8 Å. The distance between HBA2 and Grp1 will be in the range of 6.5 to 11.0 Å. The distance between Grp2 and Grp3 will be in the range of about 4.0 to about 8.0 Å, preferably between about 5.5 to about 6.6 Å.

TABLE 1

Examples of Grp2 Moieties

[Structures labeled a through h]

Grp3 will occupy a region of the ATP binding site bounded by the following amino acids: Val39, Ala52, Lys54, Ile84, Gln105, Asp106, Leu156, and Cys166. One of the positions ortho to the hydrogen bond donor HBD1 will be either unsubstituted or substituted with a relatively small group such as an aliphatic group, mono- or dialkylamino, alkoxy, or thioalkyl having one to four carbons or a halogen such as chlorine. Ideally, Grp3 will be capable of orienting in the binding pocket such that HBD1 can form a hydrogen bond with the sidechain carbonyl of Gln105. Examples of suitable Grp3 moieties are shown in Table 2. The distance between Grp3 and Grp1 is in the range of about 5.0 to 12.0 Å, preferably between about 6.0 to 10.0 Å, and most preferably between about 7.2 to 8.2 Å. The distance between Grp3 and Grp2 is in the range of about 4.0 to 8.0 Å, preferably between 5.5 to 6.6 Å. The distance between HBD1 and Grp1 is in the range of about 7.5 to 11.0 Å, preferably between about 9.0 and 10.0 Å. The distance between HBD1 and Grp2 is in the range of about 6.5 to 8.5 Å, preferably between about 7.2 and 8.2 Å.

TABLE 2

Examples of Grp3 Moieties

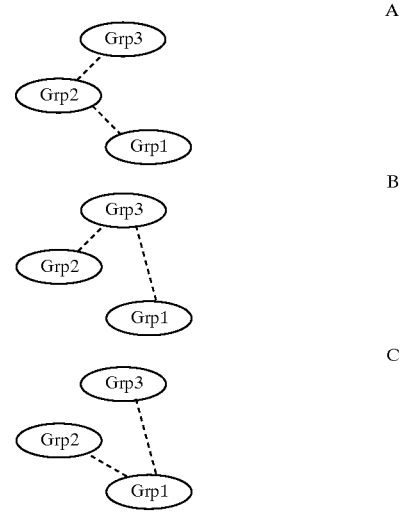

Compounds of this invention may optionally comprise an additional hydrogen bond acceptor HBA1 which is closer in distance to Grp3 than it is to Grps 1 or 2. When present, HBA1 will orient in the binding pocket so that it is capable of forming a hydrogen bond with a sidechain amino hydrogen of Lys54, or forming a water bridge to the sidechain carboxyl of Glu71, or forming a water bridge to a backbone amino hydrogen of Asp167. The HBA1 moiety is typically an sp2-hybridized oxygen such as the carbonyl of a ketone, amide or ester, or the sulfonyl of a sulfone, sulfonamide or sulfate ester. The distance between HBA1 and HBD1 is in the range of about 3.5 to 5.5 Å, preferably between about 3.9 to 4.9 Å. The distance between HBA1 and HBD2 is in the range of about 7.7 to 14.0 Å. When hydrogen bonding to Asp106, the range is between about 7.7 to 11.7 Å, preferably between about 10.2 to 11.2 Å. When hydrogen bonding to Met108, the range is between about 11.6 to 13.6 Å, preferably between about 12.1 to 13.1 Å.

Each of the groups will be connected to at least one other group by a suitable attachment means such as a valence bond, a suitable linker group or by a ring fusion. Suitable linker groups include an alkylidene chain, an aliphatic or aryl ring, —S—, —O—, —CONH—, —SO$_2$NH—, —NHCO—, —CO—, —NH—, or —NHSO$_2$—, or a combination thereof.

One process for designing a kinase inhibitor, particularly an ERK inhibitor, that embodies the present invention comprises the following steps. First, one selects a Grp2 moiety that contains a hydrogen bond acceptor HBA2 such as those shown in Table 1. Ideally, the moiety is chosen such that HBA2 would be capable of forming a direct hydrogen bond with the backbone amino hydrogen of Met108. Second, one selects a Grp1 group and a means of attachment to Grp2. It is desirable to confirm that Grp1 so attached is within the requisite distances to Grp2 and HBA2, and is capable of forming satisfactory interactions with its kinase binding site environment as described above. Confirming that the satisfactory interactions would be achievable is within the knowledge of one skilled in the art using computational methods such as those described above. In a like manner, one may build the rest of the inhibitor by selecting Grp3, and optionally HBA1, and corresponding means of attachment to provide the desired distances between groups and satisfactory interactions. The details of utilizing the method for designing an ERK inhibitor of this invention are set forth in the examples.

The compounds of this invention will usually have a molecular weight of less than about 1000 Daltons, preferably less than about 700 Daltons, and more preferably between about 400 and 600 Daltons.

It will be appreciated that Grp 1, Grp2, and Grp3 may be connected in various ways while satisfying the requisite distances described above. For example, one embodiment of this invention relates to the use of compounds wherein Grps 1 and 3 are each attached to Grp 2 as shown in structure type A below, where the dotted lines indicate an attachment means such as a valence bond. Other connectivity schemes are represented by structure types B and C:

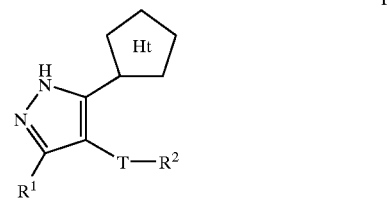

The pharmacophoric features of this invention have been used to design novel kinase inhibitors of structure type A having the general formula I:

I wherein:
Ht is a heterocyclic ring selected from pyrrol-3-yl, pyrazol-3-yl, [1,2,4]triazol-3-yl, [1,2,3]triazol-4-yl, or tetrazol-5-yl; said pyrrol-3-yl and pyrazol-3-yl having $R^3$ and $QR^4$ substituents, and said [1,2,4]triazol-3-yl and [1,2,3]triazol-4-yl substituted by either $R^3$ or $QR^4$;

$R^1$ is selected from R, F, Cl, N(R$^8$)$_2$, OR, NRCOR, NRCON(R$^8$)$_2$, CON(R$^8$)$_2$, SO$_2$R, NRSO$_2$R, or SO$_2$N(R$^8$)$_2$;

T is selected from a valence bond or a linker group;

each R is independently selected from hydrogen or an optionally substituted aliphatic group having one to six carbons;

$R^2$ is selected from hydrogen, CN, halogen, or an optionally substituted group selected from aryl, aralkyl, heteroaryl, heterocyclyl, acyclic aliphatic chain group having one to six carbons, or a cyclic aliphatic group having three to ten carbons;

$R^3$ is selected from $C_1$–$C_4$ aliphatic, OH, O($C_1$–$C_4$ aliphatic), N($C_1$–$C_4$ aliphatic)$_2$, F, Cl, or CN;

Q is a valence bond, J, or an optionally substituted $C_{1-6}$ alkylidene chain wherein up to two nonadjacent carbons of the alkylidene chain are each optionally and independently replaced by J;

J is selected from —C(=O)—, —CO$_2$—, —C(O)C(O)—, —NRCONR$^8$—, —N(R)N(R$^8$)—, —C(=O)NR$^8$—, —NRC(=O)—, —O—, —S—, —SO—, —SO$_2$—, —N(R)O—, —ON(R$^8$)—, —OC(=O)N(R$^8$)—, —N(R)COO—, —SO$_2$N(R$^8$)—, —N(R)SO$_2$—, or —N(R$^8$)—;

$R^4$ is selected from —$R^8$, —$R^5$, —$NH_2$, —$NHR^5$, —$N(R^5)_2$, or —$NR^5(CH_2)_yN(R^5)_2$;

each $R^5$ is independently selected from $R^6$, $R^7$, —$(CH_2)_y$ $CH(R^6)$ $(R^7)$, —$(CH_2)_yR^6$, —$(CH_2)_yCH(R^6)_2$, —$(CH_2)_yCH(R^7)_2$, or —$(CH_2)_yR^7$;

y is 0–6;

each $R^6$ is an optionally substituted group independently selected from an aliphatic, aryl, aralkyl, aralkoxy, heteroaryl, heteroarylalkyl, heteroarylalkoxy, heterocyclyl, heterocyclylalkyl, or heterocyclylalkoxy, group;

each $R^7$ is independently selected from an optionally substituted hydroxyalkyl, alkoxyalkyl, aryloxyalkyl, or alkoxycarbonyl; and each $R^8$ is independently selected from R or two $R^8$ on the same nitrogen taken together with the nitrogen optionally form a four to eight membered, saturated or unsaturated heterocyclic ring having one to three heteroatoms.

Compounds of formula I illustrate selected examples of compounds that were designed to contain the pharmacophoric features of the present invention. The pyrazole ring of formula I satisfies the Grp2 requirements as described above. $R^2$ is attached to Grp2 by attachment means T and satisfies the Grp1 requirements; Ht is attached to Grp2 by a valence bond and satisfies the Grp3 requirements.

More specific examples of compounds having the desired pharmacophore features are shown below for the Ht ring being pyrrol-3-yl (II-A), pyrazol-3-yl (II-B), [1,2,4]triazol-3-yl (II-C), [1,2,3]triazol-4-yl (II-D and II-E), and tetrazol-5-yl (II-F):

II-A

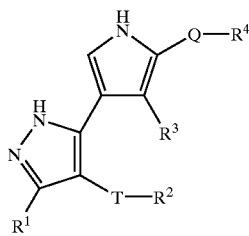

II-B

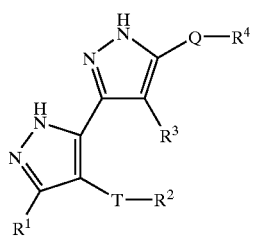

II-C

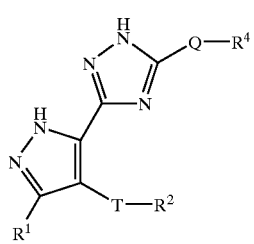

II-D

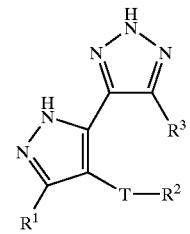

II-E

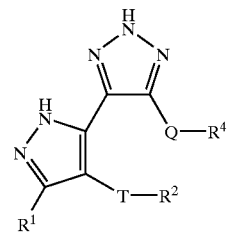

II-F

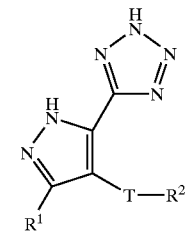

wherein $R^{1-4}$, T, and Q are as described above.

Preferred compounds of formulae II-A, II-B, II-C, II-D, II-E, and II-F include those having one or more, and most preferably all, of the following features: (a) Q is —CO—, —$CO_2$—, or —CONH—; (b) T is a valence bond; (c) $R^1$ is hydrogen or NHR; (d) $R^2$ is an optionally substituted aryl ring, more preferably an optionally substituted phenyl ring; (e) $R^3$ is hydrogen; (f) $R^4$ is selected from $R^5$, —$NHR^5$, —$N(R^5)_2$, —$NR^5R^6$, —$NHCHR^5R^6$, or —$NHCH_2R^5$; and/or (g) $R^5$ is an optionally substituted group selected from aryl, aralkyl, heteroaryl, heteroarylalkyl, heterocyclyl, heterocyclylalkyl group, $(CH_2)_yR^6$, $(CH_2)_yR^7$, or $(CH_2)_yCH(R^6)(R^7)$.

Examples of substitutions of the $R^2$ phenyl group include halo, nitro, alkoxy, and amino.

When $R^4$ is $R^5$, examples of preferred $R^5$ groups include pyrrolidin-1-yl, morpholin-1-yl, piperidin-1-yl, and piperazin-1-yl wherein each group is optionally substituted. When $R^4$ is —$NHR^5$ or —$N(R^5)_2$, preferred $R^5$ groups further include $(CH_2)_yR^6$, $(CH_2)_yR^7$, and $(CH_2)_yCH$ $(R^6)$ $(R^7)$. Examples of preferred $R^6$ and $R^7$ include pyridin-3-yl, pyridin-4-yl, imidazolyl, furan-2-yl, tetrahydrofuran-2-yl, cyclohexyl, phenyl, —$CH_2OH$, —$(CH_2)_2OH$, isopropyl, wherein each group is optionally substituted.

Exemplary structures of formula II-A, wherein $R^1$ and $R^3$ are each H, are set forth in Table 3 below.

TABLE 3

Compounds II-A

| No. II-A- | T—R² | Q—R⁴ |
|---|---|---|
| 1 | phenyl | CON(Me)₂ |
| 2 | phenyl | CO₂Et |
| 3 | 3-NO₂-phenyl | CONHNH₂ |
| 4 | phenyl | CO(pyrrolidin-1-yl) |
| 5 | phenyl | CONHCH₂(Ph) |
| 6 | 3-NO₂-phenyl | CO₂Et |
| 7 | 4-Cl-phenyl | CO₂Et |
| 8 | 4-OMe-phenyl | CO₂Et |
| 9 | 3-NH₂-phenyl | CO₂Et |
| 10 | 3-OMe-phenyl | CO₂Et |
| 11 | 4-F-phenyl | CO₂Et |
| 12 | 4-NO₂-phenyl | CO₂Et |
| 13 | 3-Cl-phenyl | CO₂Et |
| 14 | 3-F-phenyl | CO₂Et |
| 15 | phenyl | CO₂H |
| 16 | 4-NH₂-phenyl | CO₂Et |
| 17 | phenyl | CONHCH₂CH₂N(Me)₂ |
| 18 | phenyl | CONHCH₂(pyridin-3-yl) |
| 19 | phenyl | CO(morpholin-1-yl) |
| 20 | phenyl | CONH(isopropyl) |
| 21 | phenyl | CO(4-Me-piperazin-1-yl) |
| 22 | phenyl | CONHCH₂(furan-2-yl) |
| 23 | 3-OMe-phenyl | CONMe₂ |
| 24 | 3-OMe-phenyl | CO(pyrrolidin-1-yl) |
| 25 | 3-OMe-phenyl | CONHCH₂CH₂N(Me)₂ |
| 26 | 3-OMe-phenyl | CONHCH₂(pyridin-3-yl) |
| 27 | 3-OMe-phenyl | CO(morpholin-1-y1) |
| 28 | 3-OMe-phenyl | CONH(isopropyl) |
| 29 | 3-OMe-phenyl | CO(4-Me-piperazin-1-yl) |
| 30 | 3-OMe-phenyl | CONHCH₂(furan-2-yl) |
| 31 | 4-NH₂-phenyl | CO₂Et |
| 32 | H | CONMe₂ |
| 33 | H | CO(pyrrolidin-1-yl) |
| 34 | 3-(AcNH)-phenyl | CO₂Et |
| 35 | 4-(AcNH)-phenyl | CO₂Et |
| 36 | 3-(AcNH)-phenyl | CO₂Et |
| 37 | 4-(AcNH)-phenyl | CO₂Et |
| 38 | 3-Cl-phenyl | CON(H)Bn |
| 39 | 3,5-Cl₂-phenyl | CONH(2-OH-1-Ph-ethyl) |
| 40 | 5-Br-phenyl | CONH(3,4-F₂-phenyl) |
| 41 | 5-Cl-phenyl | CONH(2-OH-1-Ph-ethyl) |
| 42 | 4-OH, 3-I, 5-nitrophenyl | CONH(2-OH-1-Ph-ethyl) |
| 43 | 5-Br-phenyl | CONH(2,3-dihydro-benzofuran-5-yl) |
| 44 | 3-NH₂, 4-OH, 5-I-phenyl | CONH(2-OH-1-Ph-ethyl) |
| 45 | 5-Br-phenyl | CONH(2-OH-1-Ph-ethyl) |
| 46 | 5-Br-phenyl | CONHCH₂(3-MeO-phenyl) |
| 47 | 5-Br-phenyl | CONHCH₂(3-CF₃-phenyl) |
| 48 | 3,5-Cl₂-phenyl | CONHCH₂(pyrid-4-yl) |
| 49 | 5-CF₃-phenyl | CONH(2-OH-1-Ph-ethyl) |
| 50 | 5-Cl-phenyl | CONHCH₂Ph |
| 51 | 3,5-Cl₂-phenyl | CONHOCH₂Ph |
| 52 | 4-OH, 3-I, 5-nitrophenyl | CONHCH₂Ph |
| 53 | 5-Cl-phenyl | CONHCH₂(pyrid-4-yl) |
| 54 | 4,5-Cl₂-phenyl | CONHOCH₂Ph |
| 55 | 5-Br-phenyl | CONHCH₂(4-SO₂Me-phenyl) |
| 56 | 5-Br-phenyl | CONHNH(3-CF₃-phenyl) |

TABLE 3-continued

Compounds II-A

| No. II-A- | T—R$^2$ | Q—R$^4$ |
|---|---|---|
| 57 | 5-Cl-phenyl | CONHOCH$_2$Ph |
| 58 | 5-Br-phenyl | 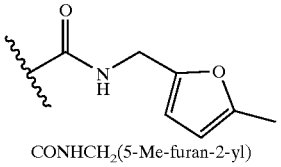 CONHCH$_2$(5-Me-furan-2-yl) |
| 59 | 5-Br-phenyl | 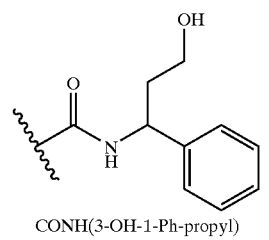 CONH(3-OH-1-Ph-propyl) |
| 60 | 5-Br-phenyl | CONHCH$_2$(2-Me-phenyl) |
| 61 | 4,5-Cl$_2$-phenyl | CONHCH$_2$(pyrid-4-yl) |
| 62 | 5-Br-phenyl | CONH(1-Ph-propyl) |
| 63 | 5-F-phenyl | CONHCH$_2$Ph |
| 64 | 4,5-Cl$_2$-phenyl | 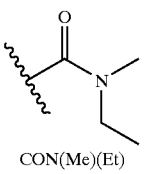 CON(Me)(Et) |
| 65 | 5-Br-phenyl | 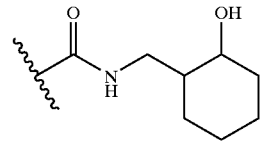 CONHCH$_2$(2-OH-cyclohexyl) |
| 66 | 3,5-Cl$_2$-phenyl | CON(Me)(Et) |
| 67 | 5-Cl-phenyl | CONHCH$_2$(pyrid-3-yl) |
| 68 | 5-Br-phenyl | CONHCH$_2$(3,5-OMe$_2$-phenyl) |
| 69 | 5-Br-phenyl | CONNCH$_2$(2-OMe-phenyl) |
| 70 | 4-F-5-Cl-phenyl | CONHCH$_2$(pyrid-4-yl) |
| 71 | 4-F-5-Cl-phenyl | CON(Me)(Et) |
| 72 | 5-Br-phenyl | CONH(2-OH-1-Ph-ethyl) |
| 73 | 5-NH$_2$-phenyl | CONHCH$_2$Ph |
| 74 | 4,5-Cl$_2$-phenyl | CONHCH$_2$(pyrid-3-yl) |
| 75 | 5-Me-phenyl | CONH(2-OH-1-Ph-ethyl) |
| 76 | 3,5-Cl$_2$-phenyl | CONHCH$_2$(pyrid-3-yl) |
| 77 | 4-F-5-Cl-phenyl | CONHOCH$_2$Ph |
| 78 | 3,5-Cl$_2$-phenyl | CONHCH$_2$(tetrahydrofuran-2-yl) |
| 79 | 5-NO$_2$-phenyl | CONHCH$_2$Ph |
| 80 | 5-F-phenyl | CONHCH$_2$(pyrid-4-yl) |
| 81 | 5-Cl-6-F-phenyl | CON(Me)(Et) |
| 82 | 2-F-3-Cl-phenyl | CONHOCH$_2$Ph |
| 83 | 5-Br-phenyl | 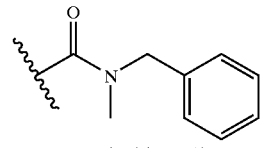 CON(Me)(CH$_2$Ph) |
| 84 | 5-Cl-phenyl | CONHCH$_2$(tetrahydrofuran-2-yl) |
| 85 | 4,5-F$_2$-phenyl | CONHOCH$_2$Ph |
| 86 | 5-Br-phenyl | CONH(3-OH-1-Ph-propyl) |

TABLE 3-continued

Compounds II-A

| No. II-A- | T—R$^2$ | Q—R$^4$ |
|---|---|---|
| 87 | 5-Br-phenyl | 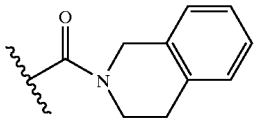 |
| 88 | 4,5-F$_2$-phenyl | CONHCH$_2$(pyrid-4-yl) |
| 89 | 5-F-phenyl | CONHOCH$_2$Ph |
| 90 | 5-Me-phenyl | CONHCH$_2$Ph |
| 91 | 5-Br-phenyl | 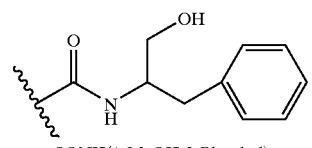<br>CONH(1-MeOH-2-Ph-ethyl) |
| 92 | 4-Cl-phenyl | CONHCH$_2$Ph |
| 93 | 5-Cl-phenyl | CON(Me)(Et) |
| 94 | 5-Br-phenyl | CONHCH$_2$(4-SO$_2$NH$_2$-phenyl) |
| 95 | 5-OH-phenyl | CONHCH$_2$Ph |
| 96 | 5-Me-phenyl | CONHCH$_2$(pyrid-4-yl) |
| 97 | Phenyl | CONHCH$_2$Ph |
| 98 | 2,5-F$_2$-phenyl | CONHCH$_2$(pyrid-4-yl) |
| 99 | 4-Cl-phenyl | CONHOCH$_2$Ph |
| 100 | 4-F-5-Cl-phenyl | CONHCH$_2$(tetrahydrofuran-2-yl) |
| 101 | 4-F-5-Cl-phenyl | CONHCH$_2$(pyrid-3-yl) |
| 102 | 5-Br-phenyl | 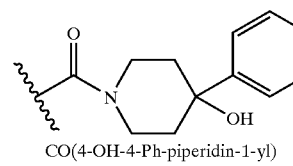<br>CO(4-OH-4-Ph-piperidin-1-yl) |
| 103 | 5,6-F$_2$-phenyl | CONHOCH$_2$Ph |
| 104 | 5-Cl-phenyl | CO(morpholin-1-yl) |
| 105 | 5-Br-phenyl | 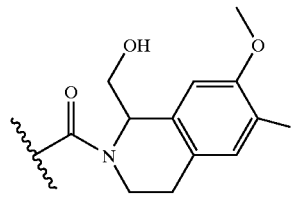 |
| 106 | 2-F-3-Cl-phenyl | CONHCH$_2$(tetrahydrofuran-2-yl) |
| 107 | 4-F-5-Cl-phenyl | CO(morpholin-1-yl) |
| 108 | 4-F-5-Cl-phenyl | CON(Me)(Et) |
| 109 | 5-Br-phenyl | CONHCH$_2$(4-NH$_2$-phenyl) |
| 110 | 5-Br-phenyl | 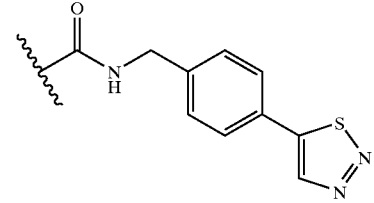 |
| 111 | 4-F-phenyl | CONHCH$_2$Ph |
| 112 | 3,5-Cl$_2$-phenyl | CO(morphalin-1-y1) |
| 113 | 2,5-F$_2$-phenyl | CONHOCH$_2$Ph |
| 114 | 2-F-3-Cl-phenyl | CONHCH$_2$(pyrid-3-yl) |
| 115 | 2-F-3-Cl-phenyl | CONHCH$_2$(pyrid-4-yl) |
| 116 | 4,5-F$_2$-phenyl | CONHCH$_2$(pyrid-3-yl) |

TABLE 3-continued

Compounds II-A

| No. II-A- | T—R² | Q—R⁴ |
|---|---|---|
| 117 | 4-OMe-phenyl | CONHCH₂Ph |
| 118 | 5-Br-phenyl | CONHCH₂(2,4,6-OMe₃-phenyl) |
| 119 | 5-F-phenyl | CONHCH₂(pyrid-3-yl) |
| 120 | 4,5-F₂-phenyl | CONHCH₂(tetrahydrofuran-2-yl) |
| 121 | 5-Cl-6-F-phenyl | ![structure: acyl-NH-CH₂-piperidine-N-Boc] |
| 122 | 5-Br-phenyl | ![structure: acyl-piperazine-N-(3-methoxyphenyl)] |
| 123 | 5-Br-phenyl | ![structure: acyl-piperidine with 4-(4-bromophenyl), 4-OH] |
| 124 | 5-Br-phenyl | CONHCH₂(2,5-OMe₂-phenyl) |
| 125 | 3,5-Cl₂-phenyl | ![structure: acyl-NH-CH₂-piperidine-N-Boc] |
| 226 | 5-Br-phenyl | ![structure: acyl-piperazine-N-(4-methylphenyl)] |
| 127 | 4,5-Cl₂-phenyl | CO(morpholin-1-yl) |
| 128 | 5-Br-phenyl | ![structure: acyl-piperazine-N-(4-fluorophenyl)] |
| 129 | 2-F-3-Cl-phenyl | CO(morpholin-1-yl) |
| 130 | 5-Br-phenyl | CONHCH₂CH₂OH |
| 131 | 5-NH₂-phenyl | CONHCH₂Ph |
| 132 | 5-MeOC(O)-phenyl | CONHCH₂Ph |
| 133 | 4-MeO-phenyl | CONHOCH₂Ph |
| 134 | phenyl | CO(pyrrolidin-1-yl) |
| 135 | 5-MeO-phenyl | CO(morpholin-1-yl) |
| 136 | 5-Cl-phenyl | CO(4-Me-piperidin-1-yl) |
| 137 | 5-NO₂-phenyl | CONH₂NH₂ |
| 138 | 5-Br-phenyl | ![structure: acyl-piperazine-N-(pyrazin-2-yl)] |

TABLE 3-continued

Compounds II-A

| No. II-A- | T—R² | Q—R⁴ |
|---|---|---|
| 139 | 5-Br-phenyl | *N-benzyl-N-(3-hydroxypropyl)amide* |
| 140 | 5-Cl-phenyl | CONHPh |
| 141 | 5,6-F₂-phenyl | CONHCH₂(pyrid-4-yl) |
| 142 | 5-Cl-phenyl | *N-(2-(1H-imidazol-4-yl)ethyl)amide* |
| 143 | phenyl | CON(Me)₂ |
| 144 | 5-OMe-phenyl | CO(pyrrolidin-1-yl) |
| 145 | 5-OMe-phenyl | CONHCH₂(pyrid-3-yl) |
| 146 | 4-F-phenyl | CONHOCH₂Ph |
| 147 | 5-OMe-phenyl | CONHCH₂(furan-2-yl) |
| 148 | 5-NO₂-phenyl | COOEt |
| 149 | phenyl | CONHCH₂(furan-2-yl) |
| 150 | phenyl | CO(morpholin-1-yl) |
| 151 | 5-Cl-phenyl | COOEt |
| 152 | 5-Br-phenyl | CONHMe |
| 153 | phenyl | CONHCH₂(pyrid-3-yl) |
| 154 | 5-OMe-phenyl | CON(Me)₂ |
| 155 | 5-Cl-phenyl | CONH(2-OH-indan-1-yl) |
| 156 | 5-Br-phenyl | *N-(pyrid-4-ylmethyl)-N-(3-hydroxypropyl)amide* |
| 157 | 5-Br-phenyl | COOEt |
| 158 | phenyl | CONH(iPr) |
| 159 | 5-OMe-phenyl | CONH(iPr) |
| 160 | 5-COOH-phenyl | CONH(iPr) |
| 161 | 5-Br-phenyl | CONHO(iPr) |
| 162 | 5-F-phenyl | COOEt |
| 163 | 5-OMe-phenyl | CO(4-Me-piperidin-1-yl) |
| 164 | 4-NH₂-phenyl | COOEt |
| 165 | 4-NO₂-phenyl | COOEt |
| 166 | pheny | CO(4-Me-piperidin-1-yl) |
| 167 | 4-Cl-phenyl | COOEt |
| 168 | 4-OMe-phenyl | COOEt |
| 169 | pheny | COOEt |
| 170 | 5-OMe-phenyl | COOEt |
| 171 | 4-F-phenyl | COOEt |
| 172 | 5-NH₂-phenyl | COOEt |

TABLE 3-continued

Compounds II-A

| No. II-A- | T—R² | Q—R⁴ |
|---|---|---|
| 173 | 5-Cl-phenyl | COOH |
| 174 | 5-Cl-phenyl | 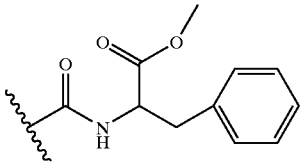 |
| 175 | 5-Cl-phenyl | 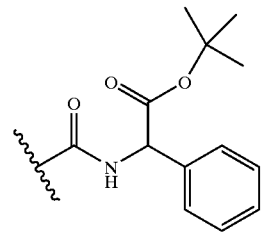 |
| 176 | 5-OMe-phenyl | CONHCH₂(pyrid-4-yl) |
| 177 | 3,5-(OMe)₂-phenyl | CONHCH₂(pyrid-4-yl) |
| 178 | 4-F-phenyl | CONHCH₂(pyrid-3-yl) |
| 179 | 4-OMe-phenyl | CONHCH₂(pyrid-3-yl) |
| 180 | 2,5-(OMe)₂-phenyl | CONHCH₂(pyrid-3-yl) |
| 181 | 2,5-F₂-phenyl | CONHCH₂(pyrid-3-yl) |
| 182 | 4-F-phenyl | CONHCH₂(tetrahydrofuran-2-yl) |
| 183 | 4-OMe-phenyl | CONHCH₂(tetrahydrofuran-2-yl) |
| 184 | 5-F-phenyl | CONHCH₂(tetrahydrofuran-2-yl) |
| 185 | 5-OMe-phenyl | CONHCH₂(tetrahydrofuran-2-yl) |
| 186 | 2,5-(OMe)₂-phenyl | CONHCH₂(tetrahydrofuran-2-yl) |
| 187 | 5,6-F₂-phenyl | CONHCH₂(tetrahydrofuran-2-yl) |
| 188 | 2,5-F₂-phenyl | CONHCH₂(tetrahydrofuran-2-yl) |
| 189 | 4-F-phenyl | CONHCH₂(1-Et-pyrrolidin-2-yl) |
| 190 | 4-OMe-phenyl | CONHCH₂(1-Et-pyrrolidin-2-yl) |
| 191 | 5-F-phenyl | CONHCH₂(1-Et-pyrrolidin-2-yl) |
| 192 | 5-OMe-phenyl | CONHCH₂(1-Et-pyrrolidin-2-yl) |
| 193 | 3,6-(OMe)₂-phenyl | CONHCH₂(1-Et-pyrrolidin-2-yl) |
| 194 | 4,5-F₂-phenyl | CONHCH₂(1-Et-pyrrolidin-2-yl) |
| 195 | 5,6-F₂-phenyl | CONHCH₂(1-Et-pyrrolidin-2-yl) |
| 196 | 3,6-F₂-phenyl | CONHCH₂(1-Et-pyrrolidin-2-yl) |
| 197 | 4-F-phenyl | CO(morpholin-1-yl) |
| 198 | 4-OMe-phenyl | CO(morpholin-1-yl) |
| 199 | 5-F-phenyl | CO(morpholin-1-yl) |
| 200 | 2,5-(OMe)₂-phenyl | CO(morpholin-1-yl) |
| 201 | 4,5-F₂-phenyl | CO(morpholin-1-yl) |
| 202 | 5,6-F₂-phenyl | CO(morpholin-1-yl) |
| 203 | 2,5-F₂-phenyl | CO(morpholin-1-yl) |
| 204 | 4-F-phenyl | CO(4-Me-piperidin-1-yl) |
| 205 | 4-OMe-phenyl | CO(4-Me-piperidin-1-yl) |
| 206 | 5-F-phenyl | CO(4-Me-piperidin-1-yl) |
| 207 | 2,5-(OMe)₂-phenyl | CO(4-Me-piperidin-1-yl) |
| 208 | 4,5-F₂-phenyl | CO(4-Me-piperidin-1-yl) |
| 209 | 5,6-F₂-phenyl | CO(4-Me-piperidin-1-yl) |
| 210 | 3,6-F₂-phenyl | CO(4-Me-piperidin-1-yl) |
| 211 | 4-Cl-phenyl | CONHCH₂(pyrid-4-yl) |
| 212 | 4,5-(OMe)₂-phenyl | CONHCH₂(pyrid-4-yl) |
| 213 | 4-benzo[1,3]dioxo-5-yl | CONHCH₂(pyrid-4-yl) |
| 214 | 4-Cl-phenyl | CONHCH₂(pyrid-3-yl) |
| 215 | 4,5-(OMe)₂-phenyl | CONHCH₂(pyrid-3-yl) |
| 216 | 4-benzo[1,3]dioxo-5-yl | CONHCH₂(pyrid-3-yl) |
| 217 | 4-Cl-phenyl | CONHCH₂(tetrahydrofuran-2-yl) |
| 218 | 4,5-(OMe)₂-phenyl | CONHCH₂(tetrahydrofuran-2-yl) |
| 219 | 4-benzo[1,3]dioxo-5-yl | CONHCH₂(tetrahydrofuran-2-yl) |
| 220 | 4-Cl-phenyl | CONHCH₂(1-Et-pyrrolidin-2-yl) |
| 221 | 4,5-Cl₂-phenyl | CONHCH₂(1-Et-pyrrolidin-2-yl) |
| 222 | 5-Cl-6-F-phenyl | CONHCH₂(1-Et-pyrrolidin-2-yl) |
| 223 | 4-F-5-Cl-phenyl | CONHCH₂(1-Et-pyrrolidin-2-yl) |
| 224 | 4,5-(OMe)₂-phenyl | CONHCH₂(1-Et-pyrrolidin-2-yl) |
| 225 | 4-benzo[1,3]dioxo-5-yl | CONHCH₂(1-Et-pyrrolidin-2-yl) |
| 226 | 3,5-Cl₂-phenyl | CONHCH₂(1-Et-pyrrolidin-2-yl) |
| 227 | 4-Cl-phenyl | CO(morpholin-1-yl) |

TABLE 3-continued

Compounds II-A

| No. II-A- | T—R² | Q—R⁴ |
|---|---|---|
| 228 | 4,5-(OMe)₂-phenyl | CO(morpholin-1-yl) |
| 229 | 4-benzo[1,3]dioxo-5-yl | CO(morpholin-1-yl) |
| 230 | 4-Cl-phenyl | CO(4-Me-piperidin-1-yl) |
| 231 | 4,5-Cl₂-phenyl | CO(4-Me-piperidin-1-yl) |
| 232 | 5-Cl-6-F-phenyl | CO(4-Me-piperidin-1-yl) |
| 233 | 4-F-5-Cl-phenyl | CO(4-Me-piperidin-1-yl) |
| 234 | 4,5-(OMe)₂-phenyl | CO(4-Me-piperidin-1-yl) |
| 235 | 4-benzo[1,3]dioxo-5-yl | CO(4-Me-piperidin-1-yl) |
| 236 | 3,5-Cl₂-phenyl | CO(4-Me-piperidin-1-yl) |
| 237 | 5,6-F₂-phenyl | CON(Me)(Et) |
| 238 | 4-F-phenyl | *structure* |
| 239 | 5-OMe-phenyl | *structure* |
| 240 | 2,5-(OMe)₂-phenyl | *structure* |
| 241 | 4,5-F₂-phenyl | *structure* |
| 242 | 5,6-F₂-phenyl | *structure* |
| 243 | 3,6-F₂-phenyl | *structure* |
| 244 | 5-MeO-phenyl | CONHOCH₂Ph |
| 245 | 2,5-(OMe)₂-phenyl | CONHOCH₂Ph |
| 246 | 5-F-phenyl | *structure* |

TABLE 3-continued
Compounds II-A
| No. II-A- | T—R² | Q—R⁴ |
|---|---|---|
| 247 | 5-MeO-phenyl | 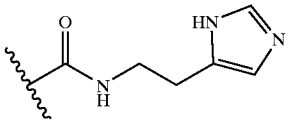 |
| 248 | 4,5-F₂-phenyl | 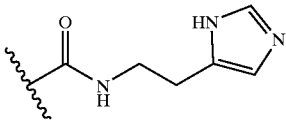 |
| 249 | 5,6-F₂-phenyl | 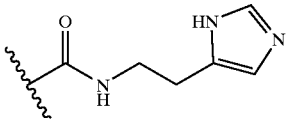 |
| 250 | 5-Cl-phenyl | 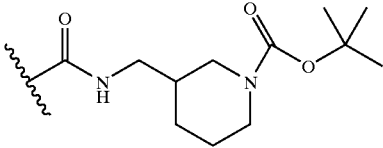 |
| 251 | 4-Cl-phenyl | 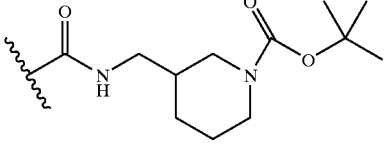 |
| 252 | 4-Cl-phenyl | 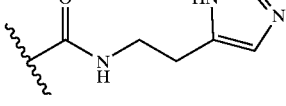 |
| 253 | 4,5-Cl₂-phenyl | 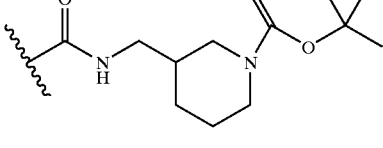 |
| 254 | 4,5-Cl₂-phenyl | 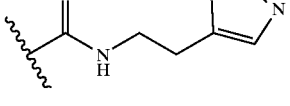 |
| 255 | 2-F-3-Cl-phenyl | 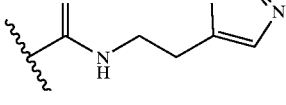 |
| 256 | 4-F-5-Cl-phenyl | 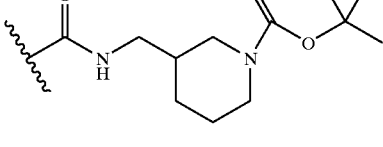 |

TABLE 3-continued
Compounds II-A
| No. II-A- | T—R² | Q—R⁴ |
|---|---|---|
| 257 | 4-F-5-Cl-phenyl | 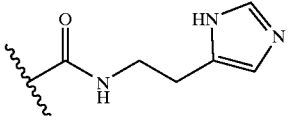 |
| 258 | 4,5-(OMe)₂-phenyl | CON(Me)(Et) |
| 259 | 4,5-(OMe)₂-phenyl | 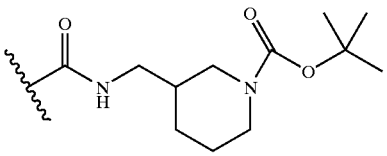 |
| 260 | 4,5-(OMe)₂-phenyl | CONHOCH₂Ph |
| 261 | 4,5-(OMe)₂-phenyl | 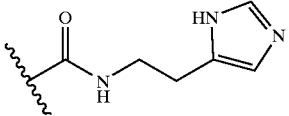 |
| 262 | 4-benzo[1,3]dioxo-5-yl | CON(Me)(Et) |
| 263 | 4-benzo[1,3]dioxo-5-yl | 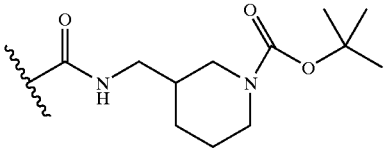 |
| 264 | 4-benzo[1,3]dioxo-5-yl | CONHOCH₂Ph |
| 265 | 4-benzo[1,3]dioxo-5-yl | 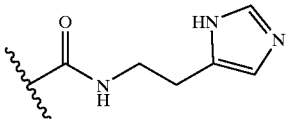 |
| 266 | 3,5-Cl₂-phenyl | 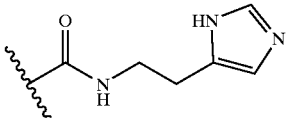 |
| 267 | 5-Br-phenyl | 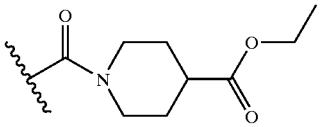 |
| 268 | 5-Br-phenyl | 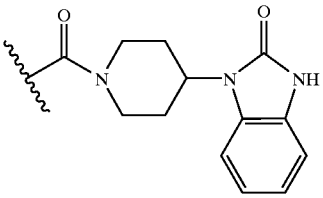 |

TABLE 3-continued
Compounds II-A
| No. II-A- | T—R² | Q—R⁴ |
|---|---|---|
| 269 | 5-Br-phenyl | 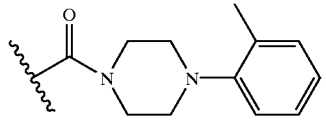 |
| 270 | 5-Br-phenyl | 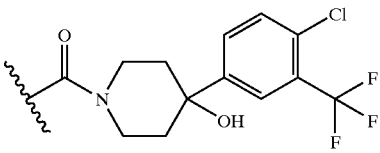 |
| 271 | 5-Br-phenyl | 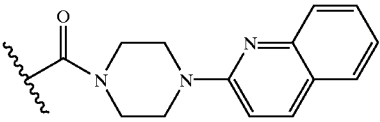 |
| 272 | 5-Br-phenyl | 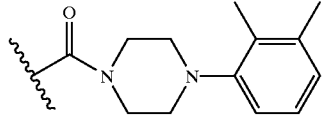 |
| 273 | 5-Br-phenyl | 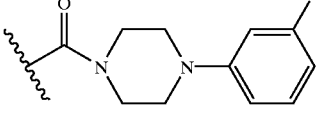 |
| 274 | 5-Br-phenyl | 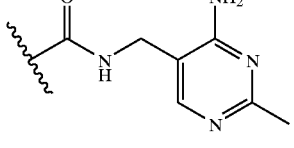 |
| 275 | 5-Br-phenyl | 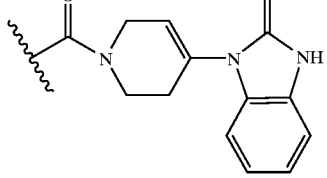 |
| 276 | 5-Br-phenyl | 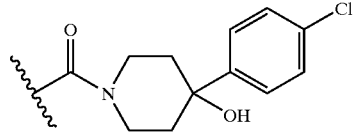 |
| 277 | 5-Br-phenyl | 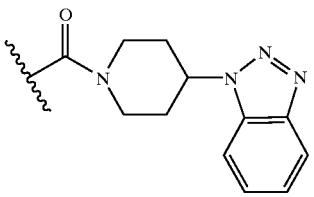 |

TABLE 3-continued

Compounds II-A

| No. II-A- | T—R² | Q—R⁴ |
|---|---|---|
| 278 | 5-Br-phenyl | [piperazine-N-linked to 3-phenyl-1,2,4-thiadiazol-5-yl, via C(=O)] |
| 279 | 5-Br-phenyl | [6-methoxy-1,2,3,4-tetrahydro-β-carbolin-2-yl, via C(=O)] |
| 280 | 5-Br-phenyl | CONH(CH₂)₂COOH |
| 281 | 5-Br-phenyl | [4-hydroxy-4-(3-trifluoromethylphenyl)piperidin-1-yl, via C(=O)] |
| 282 | 5-Br-phenyl | CONHCH₂(4-COOH-phenyl) |
| 283 | 5-Br-phenyl | [pyridoxamine-like: CONHCH₂-(3-hydroxy-2-methyl-5-hydroxymethyl-pyridin-4-yl)] |
| 284 | 5-Br-phenyl | [1,4-diazepan-1-yl connected to 4-(trifluoromethyl)pyrimidin-2-yl, via C(=O)] |
| 285 | 3-NO₂-phenyl | CONHCH₂phenyl |
| 286 | 5-Cl-phenyl | CONHCH₂(1-Et-pyrrolidin-2-yl) |
| 287 | 5-(N-Et-NHCO)-phenyl | CONHCH₂phenyl |
| 288 | 5-Br-phenyl | [N-benzyl-N-(1-phenyl-2-hydroxyethyl)amide] |

TABLE 3-continued
Compounds II-A
| No. II-A- | T—R² | Q—R⁴ |
| --- | --- | --- |
| 289 | 5-NO₂-phenyl | CONHCH₂(pyrid-4-yl) |
| 290 | 5-Br-phenyl | 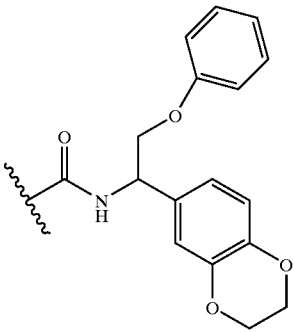 |
| 291 | 5-F-phenyl | CON(Me)(Et) |
| 292 | 5-MeO-phenyl | CON(Me)(Et) |
| 293 | 5-Br-phenyl | 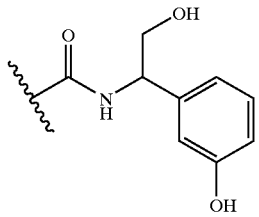 |
| 294 | 5-Br-phenyl | 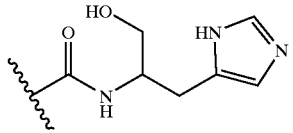 |
| 295 | 5-Br-phenyl | 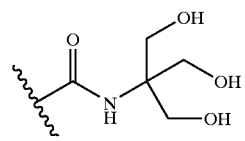 |
| 296 | 5-Br-phenyl | 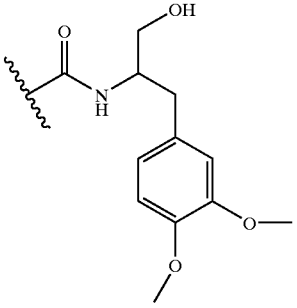 |
| 297 | phenyl | CONH(CH₂)₂NMe₂ |
| 298 | 5-MeO-phenyl | CONH(CH₂)₂NMe₂ |
| 299 | 5-Br-phenyl | CONHCH₂phenyl |

TABLE 3-continued
Compounds II-A
| No. II-A- | T—R² | Q—R⁴ |
|---|---|---|
| 300 | 3-Cl-phenyl | 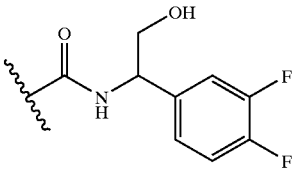 |
| 301 | 3-Cl-phenyl | 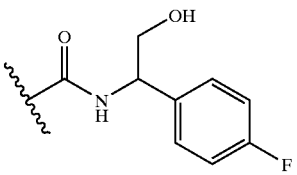 |
| 302 | 3-Cl-phenyl | 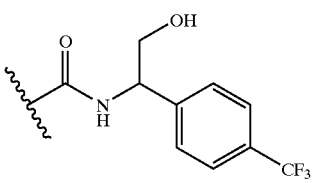 |
| 303 | 3-Cl-phenyl | 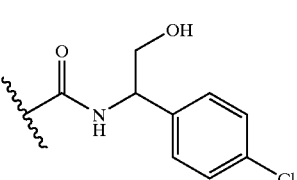 |
| 304 | 3-Cl-phenyl | 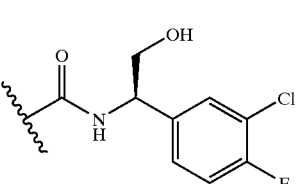 |
| 305 | 3-Cl-phenyl | 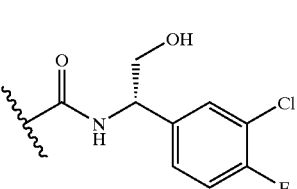 |
| 306 | 3-Cl-phenyl | 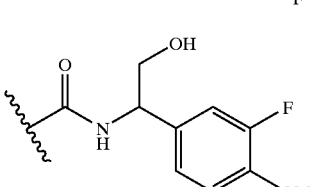 |
| 307 | 3-Cl-phenyl | 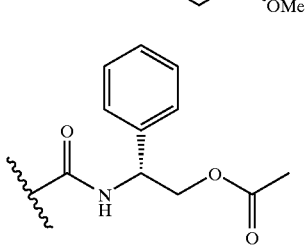 |

TABLE 3-continued

Compounds II-A

| No. II-A- | T—R² | Q—R⁴ |
|---|---|---|
| 308 | 3-Cl-phenyl | (S)-phenyl-CH(NHC(O)~)-CH₂-O-C(O)-OMe |
| 309 | 3-Cl-phenyl | 1-(4-fluoro-3-methoxyphenyl)-2-hydroxyethyl-NHC(O)~ |
| 310 | 3,5-Cl₂-phenyl | (S)-1-(3-chloro-4-fluorophenyl)-2-hydroxyethyl-NHC(O)~ |
| 311 | 3-Br-5-CF₃-phenyl | (S)-2-hydroxy-1-phenylethyl-NHC(O)~ |
| 312 | 3-Cl-phenyl | 1-(3,5-dichlorophenyl)-2-hydroxyethyl-NHC(O)~ |
| 313 | 3,5-Cl₂-phenyl | 1-(3-chloro-4-fluorophenyl)-2-hydroxyethyl-NHC(O)~ |
| 314 | 3-Cl-4-CN-phenyl | 2-hydroxy-1-phenylethyl-NHC(O)~ |

TABLE 3-continued

Compounds II-A

| No. II-A- | T—R² | Q—R⁴ |
|---|---|---|
| 315 | 3-Cl-4-CH₂OH-phenyl | phenyl-CH(CH₂OH)-NH-C(O)- |
| 316 | 3-Cl-4-CH₂NH₂-phenyl | phenyl-CH(CH₂OH)-NH-C(O)- |
| 317 | 3-Cl-4-(CH₃C(O)NHCH₂)-phenyl | phenyl-CH(CH₂OH)-NH-C(O)- |
| 318 | 3-Cl-4-(morpholinomethyl)-phenyl | phenyl-CH(CH₂OH)-NH-C(O)- |
| 319 | 3-Cl-4-(CH₃NHC(O)NHCH₂)-phenyl | phenyl-CH(CH₂OH)-NH-C(O)- |
| 320 | 3-Cl-4-(CH₃OC(O)NHCH₂)-phenyl | phenyl-CH(CH₂OH)-NH-C(O)- |
| 321 | 3-Cl-4-(CH₃CH₂S(O)₂NHCH₂)-phenyl | phenyl-CH(CH₂OH)-NH-C(O)- |

TABLE 3-continued

Compounds II-A

| No. II-A- | T—R² | Q—R⁴ |
|---|---|---|
| 322 | (MeOCH₂, Cl-substituted phenyl) | (NHC(O)— CH(Ph)CH₂OH) |
| 323 | CH₂Ph | CON(Me)₂ |
| 324 | cyclopentylmethyl | CO₂NHCH₂Ph |
| 325 | isopropyl | CN |
| 326 | 3-Cl-phenyl | NHCOCH₂Ph |
| 327 | 3-Cl-phenyl | NHSO₂-morpholin-1-yl |
| 328 | 3-Cl-phenyl | NHCONHCH₂Ph |
| 329 | 3-Cl-phenyl | NHCO₂-tetrahydrofuran-2-yl |
| 330 | CH₂Ph | CONHCH₂Ph |
| 331 | Me | CONHCH₂Ph |
| 332 | isopropyl | CONHCH₂Ph |
| 333 | H | CON(Me)₂ |

Exemplary structures of formulae II-B, II-C, II-D, and II-F, wherein $R^1$ and $R^3$ are each H and T is a valence bond, are set forth in Table 4 below.

TABLE 4

Compounds II-B, II-C, II-D, and II-F

| No. | Structure |
|---|---|
| II-B-1 | (pyrazole-carboxamide with dihydrobenzofuran and chloro-dimethylaminomethyl-phenyl-pyrazole) |
| II-B-2 | (pyrazole-carboxamide with pyridin-4-ylmethyl and chloro-hydroxymethyl-phenyl-pyrazole) |
| II-B-3 | (pyrazole-carboxamide with pyridin-4-ylmethyl and CF₃, OH phenyl-pyrazole) |
| IIB-4 | (pyrazole-carboxamide with 3,4-difluorobenzyl and hydroxypyridinyl-pyrazole) |

TABLE 4-continued

Compounds II-B, II-C, II-D, and II-F

| No. | Structure |
|---|---|
| II-B-5 | 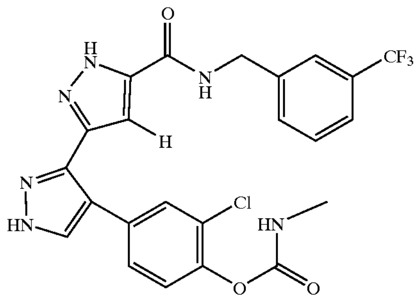 |
| II-B-6 | 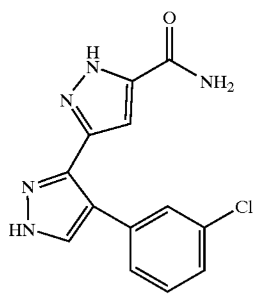 |
| II-B-7 | 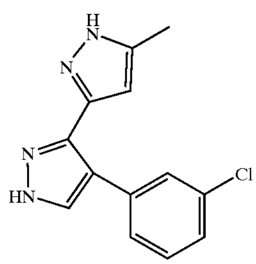 |
| II-B-8 | 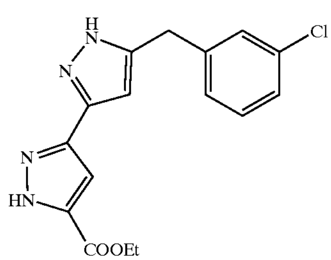 |
| II-C-1 | 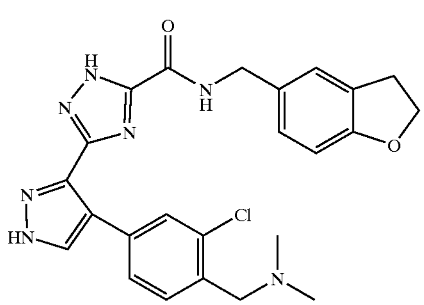 |
| II-C-2 | 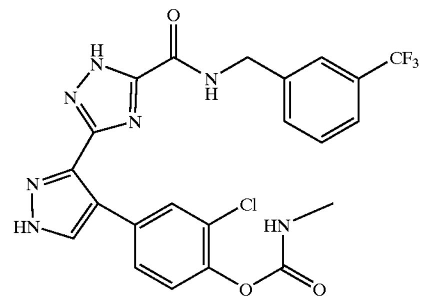 |
| II-C-3 | 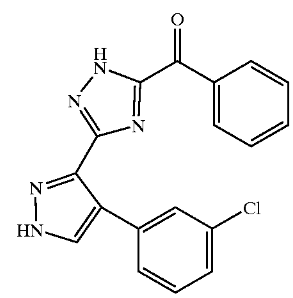 |
| II-D-1 | 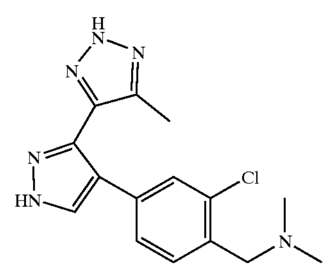 |
| II-D-2 | 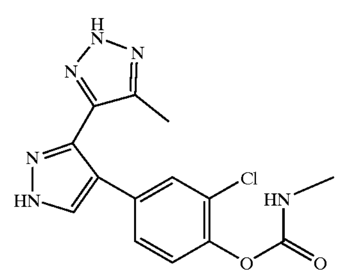 |
| II-D-3 | 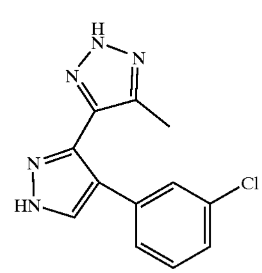 |

TABLE 4-continued

Compounds II-B, II-C, II-D, and II-F

| No. | Structure |
|---|---|
| II-D-4 | 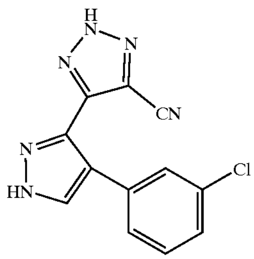 |
| II-F-1 | 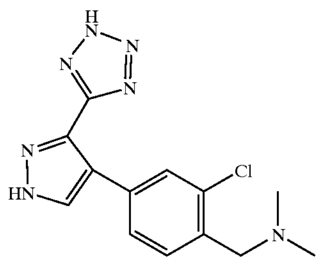 |
| II-F-2 | 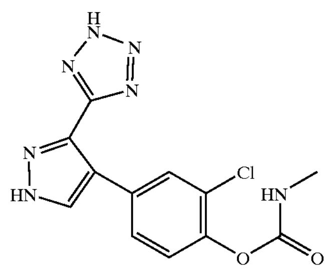 |
| II-F-3 | 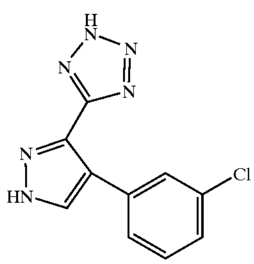 |

It will be apparent to one skilled in the art that certain compounds of this invention may exist in tautomeric forms, all such tautomeric forms of the compounds being within the scope of the invention. Examples of tautomeric forms of this invention include, but are not limited to, the tautomers shown below.

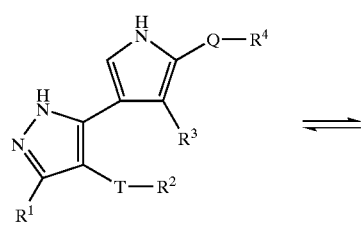
⇌
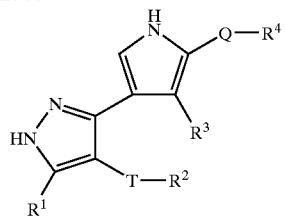

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are within the scope of this invention.

Other examples of compounds having the desired pharmacophore features are shown below for the Ht ring being pyrrol-3-yl (III-A), pyrazol-3-yl (III-B), [1,2,4]triazol-3-yl (III-C), [1,2,3]triazol-4-yl (III-D and III-E), and tetrazol-5-yl (III-F):

III-A

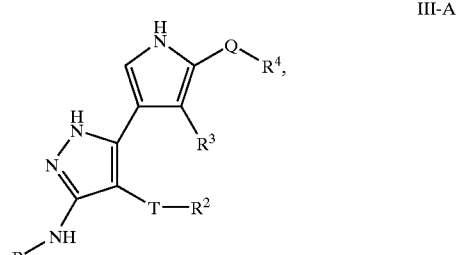

III-B

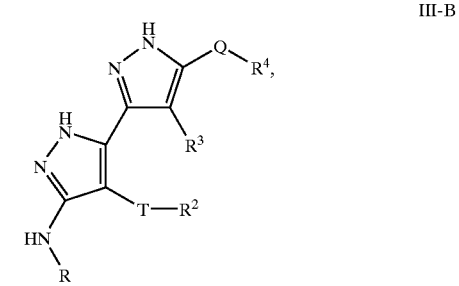

III-C

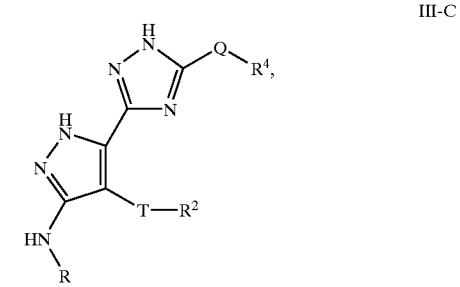

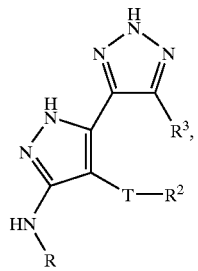

III-D

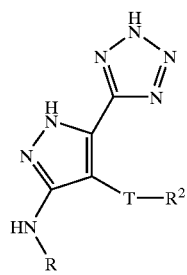

III-F

III-E wherein T, R, $R^2$, and $R^4$ are as described above.

Preferred compounds of formulae III-A, III-B, Ill-C, III-D, III-E, and III-F include those having one or more, and most preferably all, of the following features: (a) Q is —CO—, —CO$_2$—, or —CONH—; (b) T is a valence bond; (c) $R^2$ is an optionally substituted aryl ring, more preferably an optionally substituted phenyl ring; (d) $R^3$ is hydrogen; (e) $R^4$ is selected from $R^5$, —NHR$^5$, —N(R$^5$)$_2$, —NR$^5$R$^6$, —NHCHR$^5$R$^6$, or —NHCH$_2$R$^5$; and/or (f) $R^5$ is an optionally substituted group selected from aryl, aralkyl, heteroaryl, heteroarylalkyl, heterocyclyl, heterocyclylalkyl group, (CH$_2$)$_y$R$^6$, (CH$_2$)$_y$R$^7$, or (CH$_2$)$_y$CH(R$^6$) (R$^7$).

Exemplary compounds of formula III-A, wherein $R^3$ is H and T is a valence bond, are set forth in Table 5 below.

TABLE 5

Compounds III-A

| No. III-A- | R | $R^2$ | Q—$R^4$ |
|---|---|---|---|
| 1 | H | phenyl | CON(Me)$_2$ |
| 2 | H | phenyl | CO$_2$Et |
| 3 | H | 3-NO$_2$-phenyl | CONHNH$_2$ |
| 4 | H | phenyl | CO(pyrrolidin-1-yl) |
| 5 | Me | phenyl | CONHCH$_2$(Ph) |
| 6 | H | 3-NO$_2$-phenyl | CO$_2$Et |
| 7 | H | 4-Cl-phenyl | CO$_2$Et |
| 8 | Me | 4-OMe-phenyl | CO$_2$Et |
| 9 | H | 3-NH$_2$-phenyl | CO$_2$Et |
| 10 | H | 3-OMe-phenyl | CO$_2$Et |
| 11 | H | 4-F-phenyl | CO$_2$Et |
| 12 | H | 4-NO$_2$-phenyl | CO$_2$Et |
| 13 | Et | 3-Cl-phenyl | CO$_2$Et |
| 14 | H | 3-F-phenyl | CO$_2$Et |
| 15 | H | phenyl | CO$_2$H |
| 16 | Me | 3-Cl-phenyl | CONHCH$_2$(pyridin-4-yl) |
| 17 | H | 5-Cl-phenyl | (indanyl-hydroxy amide structure) |
| 18 | H | 5-F-phenyl | CONHCH$_2$(tetrahydrofuran-2-yl) |
| 19 | Me | 5,6-F$_2$-phenyl | CO(4-Me-piperidin-1-yl) |
| 20 | H | 4-Cl-phenyl | CONHCH$_2$(pyrid-4-yl) |

TABLE 5-continued

Compounds III-A

| No. III-A- | R | R² | Q—R⁴ |
|---|---|---|---|
| 21 | H | 4,5-(OMe)₂-phenyl | amide linked to ethyl-imidazole (histamine-like) |
| 22 | Me | 4,5-Cl₂-phenyl | amide linked to CH₂-(N-Boc-piperidin-3-yl) |
| 23 | H | 3-Cl-phenyl | amide of (S)-phenylglycinol O-acetate |
| 24 | H | 3-Cl-phenyl | amide of 1-(3,5-dichlorophenyl)-2-hydroxyethylamine |
| 25 | Me | 3,5-Cl₂-phenyl | amide of 1-(3-chloro-4-fluorophenyl)-2-hydroxyethylamine |
| 26 | H | 4-(ethylsulfonylaminomethyl)-3-chloro-phenyl | amide of 2-hydroxy-1-phenylethylamine |

Exemplary compounds of formula III-B, III-C, III-D, and III-F, wherein R³ is H and T is a valence bond, are set forth in Table 6 below.
TABLE 6
Compounds III-B, III-C, III-D, and III-F
| No. | Structure |
|---|---|
| III-B-1 | 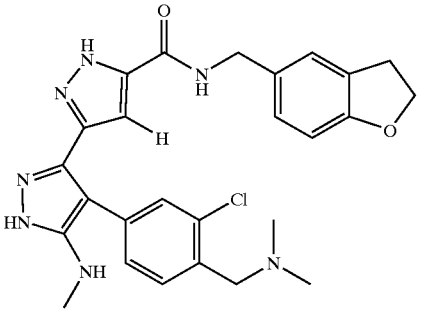 |
| III-B-2 | 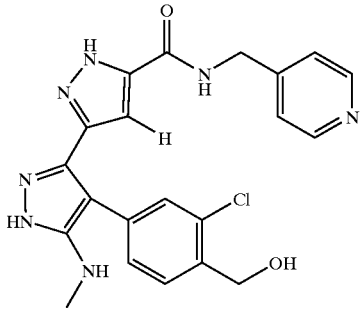 |
| III-B-3 | 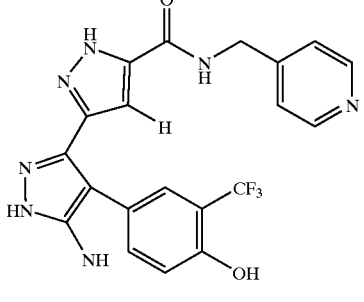 |
| III-B-4 | 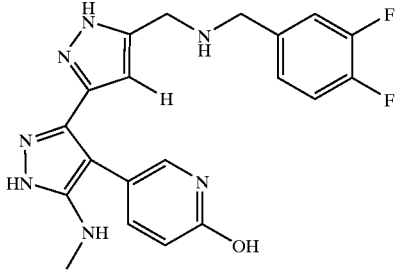 |
| III-B-5 | 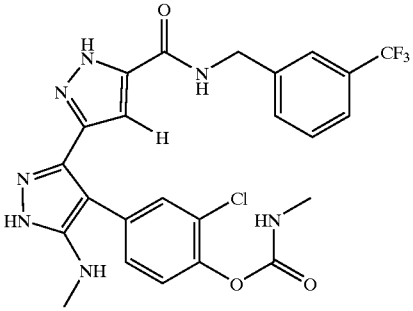 |
| III-C-1 | 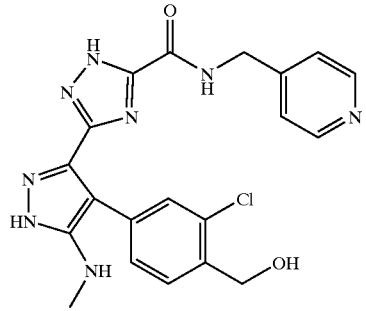 |
| III-C-2 | 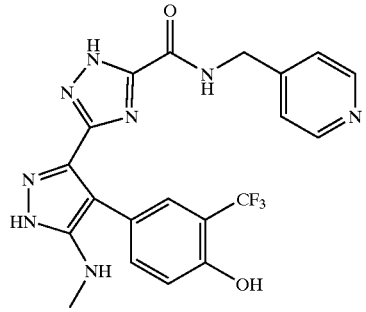 |
| III-C-3 | 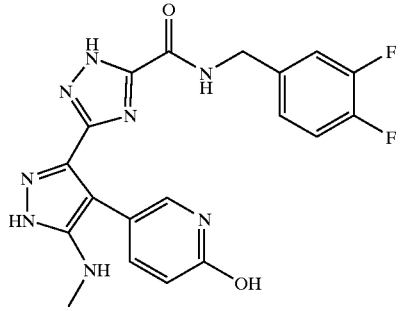 |

TABLE 6-continued

Compounds III-B, III-C, III-D, and III-F

| No. | Structure |
|---|---|
| III-D-1 | 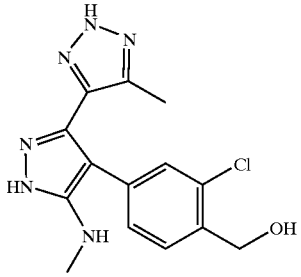 |
| III-D-2 | 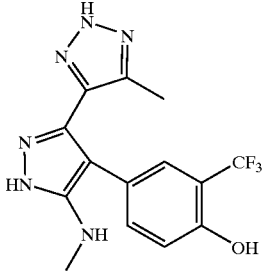 |
| III-F-1 | 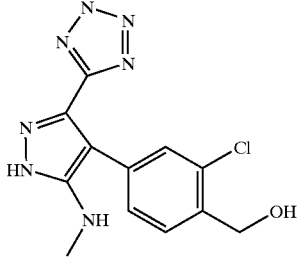 |
| III-F-2 | 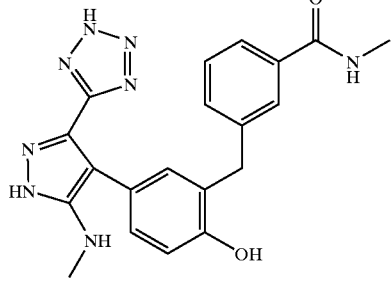 |
| III-F-3 | 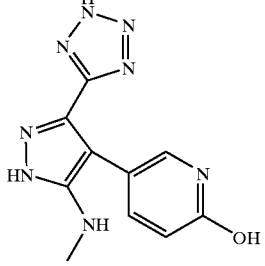 |

Compounds used in this invention may be prepared in general by methods known to those skilled in the art, such as illustrated by the general Schemes I–VI below.

Scheme I

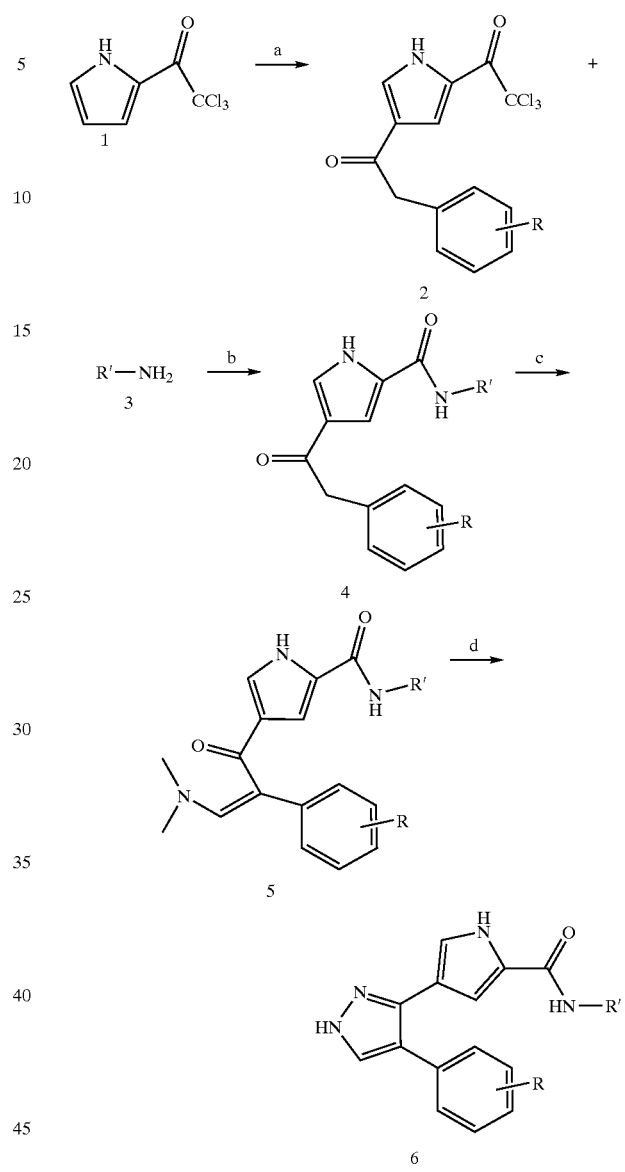

Reagents and conditions:
(a) PhCH$_2$COCl, AlCl$_3$, CH$_2$Cl$_2$, 2 hours, RT
(b) DMF, 24 hrs, room temperature
(c) (Me$_2$N)$_2$—Ot—Bu, THF, 24 hrs, room temperature
(d) H$_2$NNH$_2$, EtOH, 12 hours, reflux Scheme I above shows the general synthetic method that was used for preparing compounds of formula II-A of this invention. In step (a), the optionally substituted benzoyl chloride was combined with compound 1 in dichloromethane and aluminum trichloride to form compound 2. A wide variety of substitutions on the phenyl ring are amenable to this reaction. Examples of suitable R$^2$ groups include, but are not limited to, those set forth in Table 3 above.

The formation of amide 4 was achieved by treating compound 2 with each of a variety of amines 3 in DMF. When amine 3 was a primary amine, the reaction proceeded at ambient temperature. When amine 3 was a secondary amine, the reaction was heated at 50° C. to achieve complete reaction and afford amide 4.

The formation of enamine 5 at step (c) was achieved by treating amide 4 with (Me$_2$N)$_2$-Ot-Bu at ambient temperature. Alternatively, the reaction to form enamine 5 at step (c) was also achieved by using dimethylformamide-dimethylacetal (DMF-DMA). The reaction using DMF-DMA requires elevated temperature to afford enamine 5 whereas using (Me$_2$N)$_2$-OtBu has the advantage of proceeding at ambient temperature to afford the enamine 5 in higher purity.

The formation of the pyrazole compound 6 at step (d) was achieved by the treatment of enamine 5 with hydrazine hydrate at elevated temperature. The compounds of formula II-A synthesized by this method, as exemplified in Table 3, were isolated by preparatory HPLC (reverse phase, 10→90% MeCN in water over 15 minutes). The details of the conditions used for producing these compounds are set forth in the Examples.

Compounds of formula II-B may be prepared according to a modified method of Finar, I. L., J. Chem. Soc., (1955), pp. 1205, as shown in Scheme II below for the preparation of compound II-B-6.

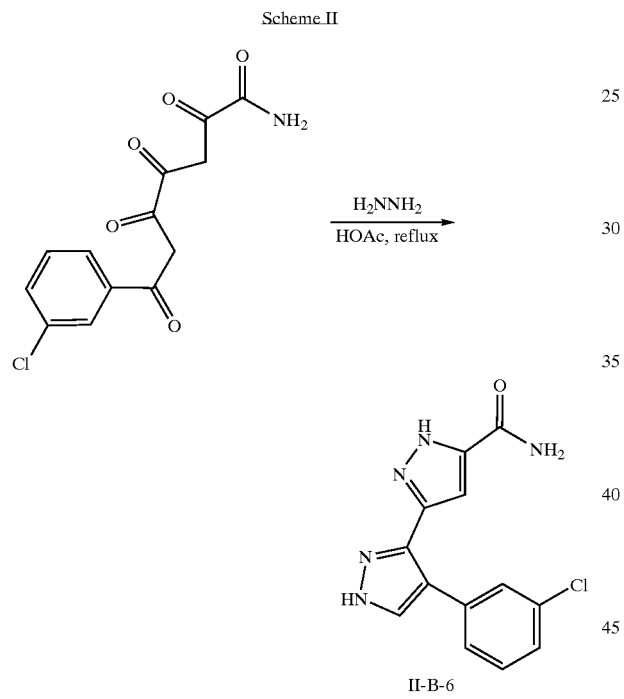

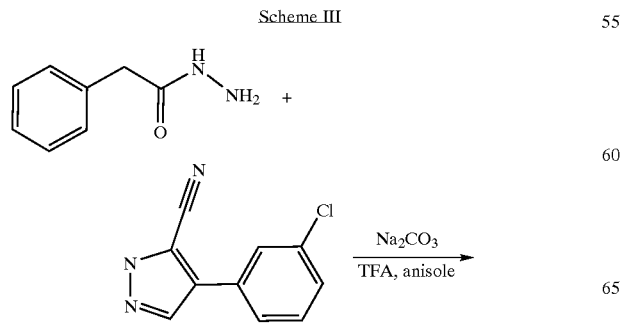

Compounds of formula II-C may be prepared according to the methods of Clitherow, J. W., et al, Bioorg. Med. Chem. Lett., (1996) pp. 833–838, as shown in Scheme III below for the preparation of compound II-C-3.

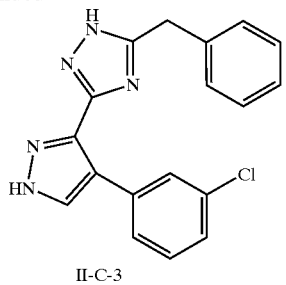

II-C-3

Compounds of formula II-D may be prepared according to the methods of Beck, G., et al, Chem. Ber., (1973) pp. 106, as shown in Scheme IV below for the preparation of compound II-D-4.

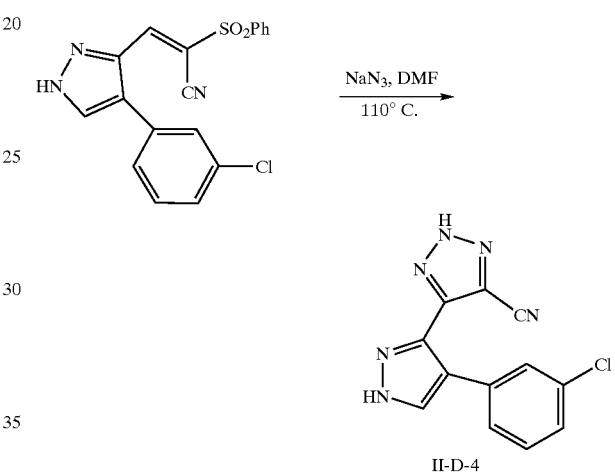

Compounds of formula II-F may be prepared according to the methods of Kaltenbronn, J. S., et al, Eur. J. med. Chem., (1997) pp. 425–431, and Norman, M. H., et al, (1995) pp. 4670–4678, as shown in Scheme V below for the preparation of compound II-F-3.

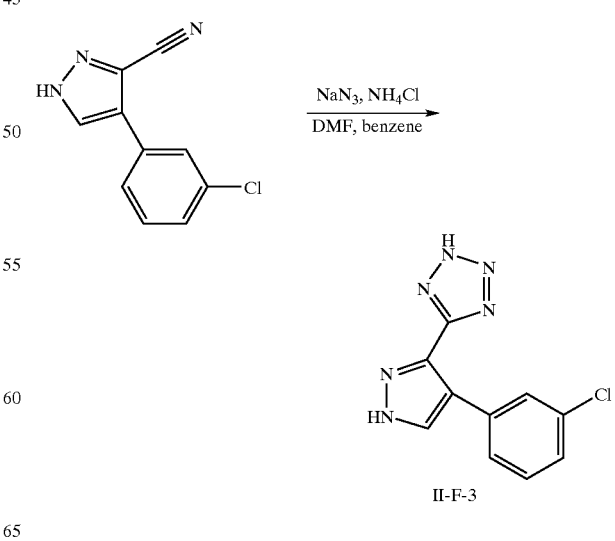

Compounds of formula III-A may be prepared in general according to the methods of Jira, T., et al, *Pharmazie,* pp.

401–406 (1994) as shown in Scheme VI below for the synthesis of compound III-A-16.

Scheme VI

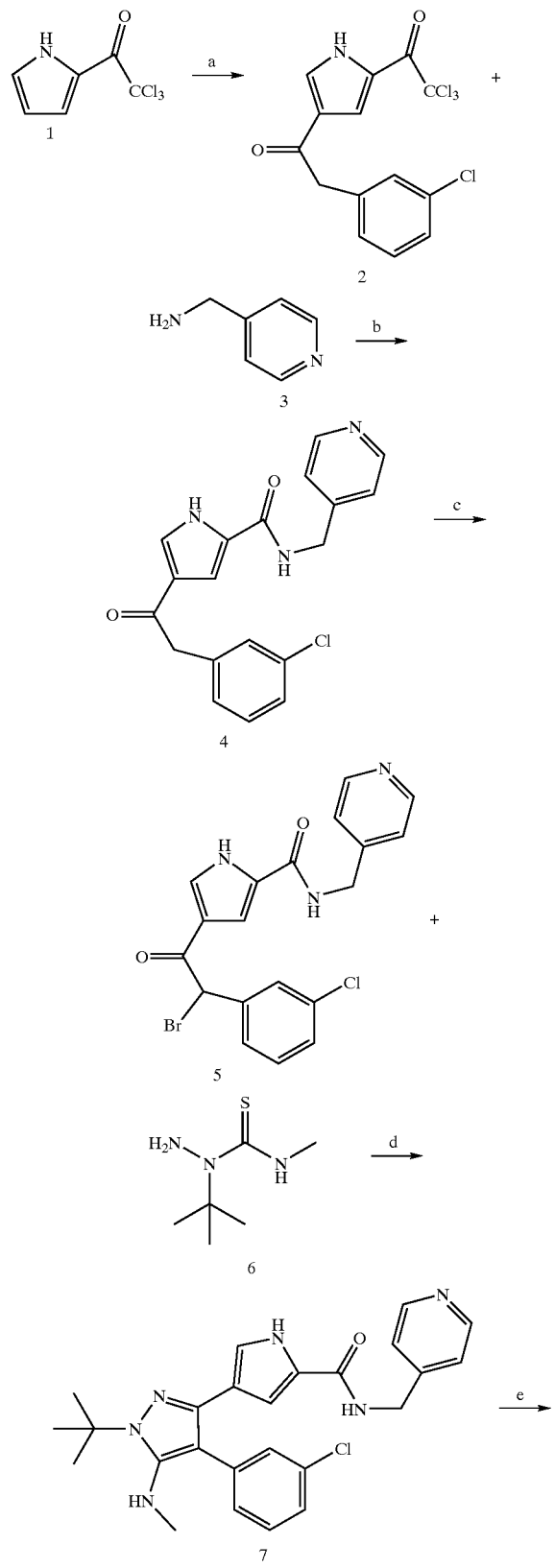

-continued

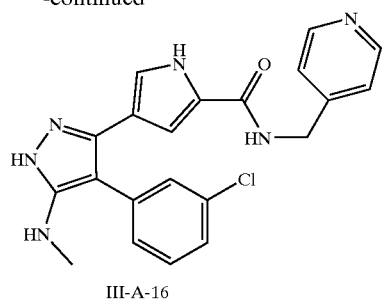

III-A-16

Reagents and conditions:
(a) 3-Cl—PhCH₂COCl, AlCl₃, CH₂Cl₂, 2 hours, RT
(b) DMF, 24 hrs, room temperature
(c) NBS, CCl₄, reflux
(d) iPrOH, reflux
(e) formic acid, reflux, 2 hours.

Using compound III-A-16 as an example, Scheme VI above shows a general synthetic method that may be used for preparing compounds of formula III-A. This method is modified from that of Jira, T., et al, *Pharmazie*, pp. 401–406 (1994). Compounds of formula III-A may also be prepared by methods similar to those of Woller, J., et al, *Pharmazie*, pp. 937–940 (1996), Rychmans, T., et al, *Tetrahedron*, pp. 1729–1734 (1997), and Tupper, D. E., et al, *Synthesis, pp.* 337–341 (1997).

According to another embodiment, the invention provides a method of inhibiting kinase activity in a biological sample. This method comprises the step of contacting said biological sample with a compound of this invention.

The term "biological sample", as used herein includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administrating said compound (or composition comprising said compound) to a mammal."

One aspect of this invention relates to a method for treating a disease state in mammals that is alleviated by treatment with a protein kinase inhibitor, especially an ERK inhibitor, which method comprises administering to a mammal in need of such a treatment a therapeutically effective amount of a compound having the pharmacophoric features of this invention.

The method is particularly useful for treating a disease state that is alleviated by the use of an inhibitor of one or more enzymes selected from ERK or JAK.

One embodiment of this method comprises administering a compound of formula I, preferably a compound of formula II-A. Another embodiment comprises administering a compound of formula III, preferably a compound of formula III-A, and most preferably, a compound listed in Tables 3–6. Pharmaceutical compositions useful for such methods are described below.

The activity of the compounds as protein kinase inhibitors, for example as ERK inhibitors, may be assayed in vitro, in vivo or in a cell line. In vitro assays include assays that determine inhibition of either the kinase activity or ATPase activity of activated ERK. Alternate in vitro assays quantitate the ability of the inhibitor to bind to ERK and may be measured either by radiolabelling the inhibitor prior to binding, isolating the inhibitor/ERK complex and determining the amount of radiolabel bound, or by running a competition experiment where new inhibitors are incubated with ERK bound to known radioligands. One may use any type or isoform of ERK, depending upon which ERK type or isoform is to be inhibited.

The protein kinase inhibitors, particularly ERK inhibitors, or pharmaceutical salts thereof may be formulated into pharmaceutical compositions for administration to animals or humans. These pharmaceutical compositions, which comprise an amount of the protein inhibitor effective to treat or prevent an ERK-mediated condition and a pharmaceutically acceptable carrier, are another embodiment of the present invention.

The term "ERK-mediated condition", as used herein means any disease or other deleterious condition in which ERK is known to play a role. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic reactions including asthma, inflammation, neurological disorders and hormone-related diseases. The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of ERK inhibitor that may be combined with the carrier materials to produce a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

The protein kinase inhibitors of this invention, or pharmaceutical salts thereof, may be formulated into pharmaceutical compositions for administration to animals, especially mammals or humans. These pharmaceutical compositions effective to treat or prevent a protein kinase-mediated condition which comprise the protein kinase inhibitor in an amount sufficient to detectably inhibit protein kinase activity and a pharmaceutically acceptable carrier, are another embodiment of the present invention. The term "detectably inhibit", as used herein means a measurable change in activity between a sample containing said inhibitor and a sample containing only a protein kinase.

According to another embodiment, the invention provides methods for treating or preventing a ERK-mediated condition comprising the step of administering to a patient one of the above-described pharmaceutical compositions. The term "patient", as used herein, means an animal, preferably a mammal, and most preferably a human.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer, stroke, diabetes, hepatomegaly, cardiomegaly, Alzheimer's disease, cystic fibrosis, and viral disease, or any specific disease or disorder described above.

The kinase inhibitors of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a composition comprising a kinase inhibitor. Compositions comprising a kinase inhibitor of this invention and a suitable carrier or coating are another embodiment of the present invention.

Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a kinase inhibitor of this invention are another embodiment of the present invention.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

In order that the invention described herein may be more fully understood, the following examples are set forth. It should be understood that these examples are for illustrative purposes only and are not to be construed as limiting this invention in any manner.

EXAMPLES

Example 1

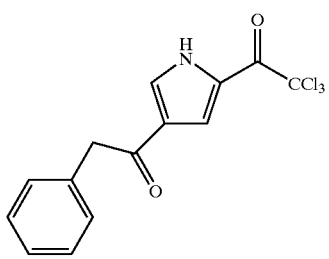

2,2,2-Trichloro-1-(4-phenylacetyl-1H-pyrrol-2-yl)-ethanone (1): In a dry flask, phenylacetyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided compound 1 in 60% yield. $^1$H NMR (CDCl$_3$) □4.0 (s, 2H), 7.1–7.35 (m, 7H), 9.7 (br s, NH). HPLC using method B (as described below for Example 5) provided a retention time of 4.9 minutes. LC/MS (M+1) 330.2, (M−1) 328.1.

Example 2

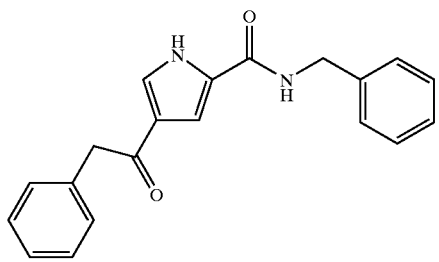

4-Phenylacetyl-1H-pyrrole-2-carboxylic acid benzylamide (2): To a solution of compound 1 (1 equivalent) in DMF, at ambient temperature, was added benzylamine (1.2 equivalents). After 24 hours, the solvent was evaporated and the crude product 2 was utilized without purification. HPLC using method B (as described below for Example 5) provided a retention time of 3.8 minutes. FIA/MS (M+1) 319.3, (M−1) 317.2.

Example 3

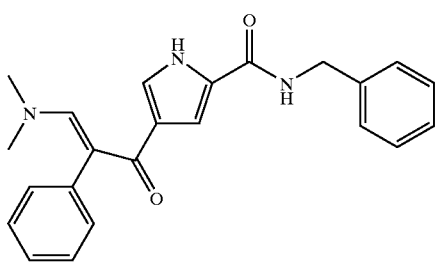

4-(3-Dimethylamino-2-phenyl-acryloyl)-1H-pyrrole-2-carboxylic acid benzylamide (3): To a solution of compound 2 (1 equivalent) in THF, at ambient temperature, was added (Me$_2$N)$_2$CHOt-Bu (3 equivalents). After 24 hours, the solvent was evaporated and the crude product 3 was utilized without purification. $^1$H NMR (CDCl$_3$) □4.4 (s, 2H), 4.8 (s, NH), 6.8–7.4 (m, 13H).

Example 4

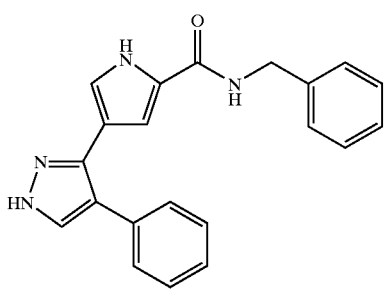

4-(4-phenyl-1H-pyrazole-3-yl)-1H-pyrrole-2-carboxylic acid benzylamide (II-5): To a solution of compound 3 (1 equivalent) in ethanol, at ambient temperature, was added hydrazine hydrate (3 equivalents) and the resulting mixture heated at reflux. After 12 hours, the solvent was evaporated and the crude product purified by preparatory HPLC (reverse phase; 10→90% MeCN in water; 15 minutes) to afford the desired compound II-5. LC/MS (M+1) 343.3, (M−1) 341.2.

Example 5

We have prepared other compounds of formula II by methods substantially similar to those described in the above Examples 1–4 and as illustrated in Scheme I. The characterization data for these compounds is summarized in Table 7 below and includes LC/MS, HPLC, and $^1$H NMR data.

For compounds where the HPLC Method is designated as "A", the following method was utilized: a gradient of water:MeCN, 0.1% TFA (95:5→0:100) was run over 22 minutes at 1 mL/min and 214 nm. For compounds where the HPLC Method is designated as "B", the following method was utilized: a gradient of water:MeCN, 0.1% TFA (90:10→0:100) was run over 8 minutes at 1 mL/min and 214 nm. Each of methods A and B utilize the YMC ODS-AQ 55 120A column with a size of 3.0×150 mm. The term "$T_{ret}$ (min)" refers to the retention time, in minutes, associated with the compound using the designated HPLC method.

Where applicable, $^1$H NMR data is also summarized in Table 7 below wherein "Y" designates $^1$H NMR data is available and was found to be consistant with structure. Compound numbers correspond to the compound numbers listed in Table 3.

TABLE 7

Characterization Data for Selected Compounds

| Compound No II-A- | M + 1 | M − 1 | HPLC Method | $T_{ret}$ (min) | $^1$H NMR |
|---|---|---|---|---|---|
| 41 | 407.4 | 405.4 | A | 8.6 | Y |
| 42 | 560.2 | 558.1 | A | 9.5 | — |
| 43 | — | — | A | 10.5 | — |
| 44 | 530.3 | 528.2 | A | 6.3 | — |
| 45 | — | — | A | 9.8 | — |
| 46 | — | — | A | 10.6 | — |
| 50 | 377.4 | — | A | 10.1 | Y |
| 52 | 530.2 | 528.2 | A | 10.3 | — |
| 53 | 378.4 | 376.3 | A | 7.4 | Y |
| 56 | 490.2 | 488.1 | A | 10.8 | — |
| 58 | — | — | A | 10.46 | — |
| 59 | — | — | A | 9.1 | — |
| 63 | 361.4 | 359.3 | A | 9.5 | Y |
| 65 | — | — | A | 10.0 | — |
| 67 | 378.4 | 376.3 | A | 7.4 | Y |
| 72 | 451.5 | 449.1 | A | 10.15 | Y |
| 80 | 374.4 | 372.3 | A | 6.6 | — |
| 83 | 435.3 | 433.4 | A | 10.3 | — |
| 85 | — | — | A | 10.6 | — |
| 86 | — | — | A | 9.3 | — |
| 88 | 380.4 | 378.3 | A | 6.9 | — |
| 89 | — | — | A | 10.5 | — |
| 91 | — | — | A | 9.6 | — |
| 92 | 377.4 | 375.3 | A | 10.2 | Y |
| 94 | — | — | A | 9.0 | — |
| 97 | 342.1 | — | B | 3.8 | Y |
| 98 | 380.4 | 378.3 | A | 6.7 | — |
| 102 | — | — | A | 10.3 | — |
| 103 | — | — | A | 10.6 | — |
| 105 | — | — | A | 9.3 | — |
| 109 | — | — | A | 7.9 | — |
| 110 | — | — | A | 10.3 | — |
| 111 | 361.4 | 359.3 | A | 9.4 | Y |
| 113 | — | — | A | 10.6 | — |
| 116 | 380.2 | 378.4 | A | 6.9 | — |
| 117 | 373.4 | — | A | 9.0 | Y |
| 119 | 362.4 | 371.4 | A | 6.5 | — |
| 120 | 373.4 | 371.4 | A | 8.2 | — |
| 122 | — | — | A | 10.8 | — |
| 123 | — | — | A | 11.4 | — |
| 126 | — | — | A | 10.2 | — |
| 128 | — | — | A | 10.9 | — |
| 130 | — | — | A | 7.4 | — |
| 133 | — | — | A | 9.5 | — |
| 134 | 306.1 | — | B | 3.5 | Y |
| 135 | 353.4 | 351.4 | A | 7.7 | — |
| 137 | 313.3 | 311.2 | A | 6.4 | Y |
| 141 | 380.4 | 378.3 | A | 6.7 | — |
| 143 | 280.1 | — | B | 3.3 | Y |
| 144 | 336.4 | — | B | 3.5 | — |
| 145 | 373.4 | — | B | 2.8 | — |
| 146 | — | — | A | 10.5 | — |
| 147 | 362.4 | — | B | 3.5 | — |
| 148 | 327.3 | 325.2 | A | 9.2 | Y |
| 149 | 332.4 | — | B | 3.5 | — |
| 150 | 322.4 | — | B | 3.2 | — |
| 151 | 316.2 | 314.2 | A | 10.3 | Y |
| 152 | — | — | A | 6.6 | — |
| 153 | 323.4 | — | B | 2.3 | — |
| 154 | 343.4 | — | B | 2.8 | — |
| 158 | 294.3 | — | B | 3.4 | — |
| 159 | 335.4 | — | B | 2.7 | — |
| 161 | 389.3 | 387.2 | A | 8.9 | — |
| 162 | 300.3 | 298.2 | A | 9.5 | Y |
| 163 | 366.5 | 364.4 | B | 6.0 | — |
| 164 | 297.3 | — | A | 5.1 | Y |
| 165 | 322.3 | 325.2 | A | 9.7 | Y |
| 167 | 316.2 | 314.2 | A | 10.0 | Y |
| 168 | 312.3 | 310.2 | A | 8.6 | Y |
| 169 | 281.1 | — | B | 3.9 | Y |
| 170 | 312.3 | 310.2 | A | 9.1 | Y |
| 171 | 300.3 | 298.2 | A | 9.4 | Y |
| 172 | 297.3 | 295.7 | A | 5.5 | Y |
| 174 | 449.3 | 447.2 | A | 12.5 | Y |
| 175 | 477.3 | 475.3 | A | 14.0 | Y |
| 176 | 374.4 | 372.4 | A | 6.3 | — |
| 178 | 362.4 | 360.0 | A | 6.6 | — |
| 179 | 374.4 | 372.4 | A | 6.3 | — |
| 180 | 404.4 | 402.4 | A | 6.4 | — |
| 181 | 380.2 | 378.3 | A | 6.7 | — |
| 182 | 355.4 | 353.4 | A | 7.7 | — |
| 183 | 367.4 | 365.4 | A | 7.4 | — |
| 184 | 355.4 | 353.4 | A | 7.9 | — |
| 185 | 367.4 | 365.3 | A | 7.5 | — |
| 186 | 397.4 | 395.4 | A | 7.1 | — |
| 187 | 373.4 | 371.4 | A | 8.0 | — |
| 188 | 373.4 | 371.4 | A | 7.9 | — |
| 189 | 382.4 | 380.4 | A | 6.9 | — |
| 190 | 394.4 | 392.4 | A | 6.7 | — |
| 191 | 382.4 | 380.4 | A | 7.0 | — |
| 192 | 394.5 | 392.4 | A | 6.7 | — |
| 193 | 424.4 | 422.4 | A | 6.4 | — |
| 194 | 400.4 | 398.4 | A | 7.3 | — |
| 195 | 400.4 | 398.4 | A | 7.1 | — |
| 196 | 400.4 | 398.4 | A | 7.2 | — |
| 197 | 341.3 | 339.2 | A | 7.5 | — |
| 198 | 353.4 | 351.4 | A | 7.1 | — |
| 199 | 341.3 | 339.2 | A | 7.6 | — |
| 200 | 383.4 | 381.4 | A | 6.9 | — |
| 201 | 359.4 | 357.4 | A | 8.0 | — |
| 202 | 359.4 | 357.4 | A | 7.8 | — |
| 203 | 359.4 | 357.4 | A | 7.7 | — |
| 204 | 354.4 | 352.4 | A | 6.2 | — |
| 205 | 366.4 | 364.4 | A | 5.9 | — |
| 206 | 354.4 | .52.4 | A | 5.6 | — |
| 207 | 396.4 | 394.4 | A | 5.9 | — |
| 208 | 372.4 | 370.4 | A | 6.7 | — |
| 209 | 372.4 | 370.4 | A | 6.5 | — |
| 210 | 372.4 | 370.4 | A | 6.4 | — |
| 237 | — | — | A | 9.8 | — |
| 238 | — | — | A | 11.6 | — |
| 239 | — | — | A | 11.3 | — |
| 240 | — | — | A | 7.5 | — |
| 241 | — | — | A | 12.0 | — |

TABLE 7-continued

Characterization Data for Selected Compounds

| Compound No II-A- | M + 1 | M − 1 | HPLC Method | T_ret (min) | $^1$H NMR |
|---|---|---|---|---|---|
| 242 | — | — | A | 11.7 | — |
| 243 | — | — | A | 11.6 | — |
| 244 | 389.4 | 387.3 | A | 10.2 | — |
| 245 | — | — | A | 10.6 | — |
| 246 | 365.4 | 363.4 | A | 7.5 | — |
| 247 | — | — | A | 7.2 | — |
| 248 | — | — | A | 8.0 | — |
| 249 | — | — | A | 7.7 | — |
| 267 | — | — | A | 10.7 | — |
| 268 | — | — | A | 10.0 | — |
| 269 | — | — | A | 12.2 | — |
| 270 | — | — | A | 12.3 | — |
| 271 | — | — | A | 9.3 | — |
| 272 | — | — | A | 12.7 | — |
| 273 | — | — | A | 12.7 | — |
| 274 | — | — | A | 3.8 | — |
| 275 | — | — | A | 10.3 | — |
| 276 | — | — | A | 8.4 | — |
| 277 | — | — | A | 10.6 | — |
| 278 | — | — | A | 12.8 | — |
| 279 | — | — | A | 11.4 | — |
| 280 | — | — | A | 7.9 | — |
| 281 | — | — | A | 11.5 | — |
| 282 | — | — | A | 8.6 | — |
| 283 | — | — | A | 8.4 | — |
| 284 | — | — | A | 12.2 | — |
| 290 | — | — | A | 11.4 | — |
| 291 | — | — | A | 9.7 | — |
| 292 | — | — | A | 9.1 | — |
| 293 | 481.3 | 479.3 | A | 8.3 | — |
| 294 | 455.4 | 453.3 | A | 6.9 | — |
| 295 | — | — | A | 7.5 | — |
| 296 | — | — | A | 8.9 | — |
| 298 | 353.4 | — | B | 2.8 | — |
| 299 | 421.3 | 423.2 | A | 10.1 | — |

Example 6

Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM MgCl$_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The IC$_{50}$ was evaluated from the rate data as a function of inhibitor concentration.

Table 8 shows the results of the activity of selected compounds of this invention in the ERK2 inhibition assay. The compound numbers correspond to the compound numbers in Table 3. Compounds having an activity designated as "A" provided a K$_i$ value below 1 micromolar; compounds having an activity designated as "B" provided a K$_i$ value between 1 and 5 micromolar; and compounds having an activity designated as "C" provided a K$_i$ value greater than 5 micromolar.

TABLE 8

ERK2 Inhibitory Activity of Selected Compounds

| No. II-A- | Activity | No. II-A- | Activity | No. II-A- | Activity |
|---|---|---|---|---|---|
| 1 | A | 2 | C | 3 | A |
| 4 | A | 5 | A | 6 | A |
| 7 | C | 8 | C | 9 | C |
| 10 | C | 11 | C | 12 | C |
| 13 | A | 14 | C | 16 | C |
| 17 | C | 18 | A | 19 | A |
| 20 | A | 21 | C | 22 | A |
| 23 | A | 24 | A | 25 | C |
| 26 | A | 27 | A | 28 | A |
| 29 | C | 30 | A | 31 | C |
| 39 | A | 40 | A | 41 | A |
| 42 | A | 43 | A | 44 | A |
| 45 | A | 46 | A | 47 | A |
| 48 | A | 49 | A | 50 | A |
| 51 | A | 52 | A | 53 | A |
| 54 | A | 55 | A | 56 | A |
| 57 | A | 58 | A | 59 | A |
| 60 | A | 61 | A | 62 | A |
| 63 | A | 64 | A | I65 | A |
| 66 | A | 67 | A | 68 | A |
| 69 | A | 70 | A | 71 | A |
| 72 | A | 73 | A | 74 | A |
| 75 | A | 76 | A | 77 | A |
| 78 | A | 79 | A | 80 | A |
| 81 | A | 82 | A | 83 | A |
| 84 | A | 85 | A | 86 | A |
| 87 | A | 88 | A | 89 | A |
| 90 | A | 91 | A | 92 | A |
| 93 | A | 94 | A | 95 | A |
| 96 | A | 97 | A | 98 | A |
| 99 | A | 100 | A | 101 | A |
| 102 | A | 103 | A | 104 | A |
| 105 | A | 106 | A | 107 | A |
| 108 | A | 109 | A | 110 | A |
| 111 | A | 112 | A | 113 | A |
| 114 | A | 115 | A | 116 | B |
| 117 | B | 118 | B | 119 | B |
| 120 | B | 121 | B | 122 | B |
| 123 | B | 124 | B | 125 | B |
| 126 | B | 127 | B | 128 | B |
| 129 | B | 130 | B | 131 | B |
| 132 | B | 133 | B | 134 | B |
| 135 | B | 136 | B | 137 | B |
| 138 | B | 139 | B | 140 | B |
| 141 | B | 142 | B | 143 | B |
| 144 | B | 145 | B | 146 | B |
| 147 | B | 148 | B | 149 | B |
| 150 | B | 151 | B | 152 | B |
| 153 | B | 154 | B | 155 | B |
| 156 | B | 157 | B | 158 | B |
| 159 | B | 160 | B | 161 | C |
| 162 | C | 163 | C | 164 | C |
| 165 | C | 166 | C | 167 | C |
| 168 | C | 169 | C | 170 | C |
| 171 | C | 172 | C | 285 | B |
| 286 | C | 287 | C | 288 | B |
| 289 | C | 290 | B | 291 | C |
| 292 | C | 293 | C | 294 | C |
| 295 | C | 296 | C | 297 | C |
| 298 | C | 299 | C | | |

Example 7

ERK Inhibition Cell Proliferation Assay

Compounds were assayed for the inhibition of ERK2 by a cell proliferation assay. In this assay, a complete media was prepared by adding 10% fetal bovine serum and penicillin/- streptomycin solution to RPMI 1640 medium (JRH Biosciences). Colon cancer cells (HT-29 cell line) were added to each of 84 wells of a 96 well plate at a seeding density of 10,000 cells/well/150 □L. The cells were allowed to attach to the plate by incubating at 37° C. for 2 hours. A solution of test compound was prepared in complete media by serial dilution to obtain the following concentrations: 20 µM, 6.7 µM, 2.2 µM, 0.74 µM, 0.25 µM, and 0.08 µM. The test compound solution (50 µL) was added to each of 72 cell-containing wells. To the 12 remaining cell-containing wells, only complete media (200 µL) was added to form a control group in order to measure maximal proliferation. To the remaining 12 empty wells, complete media was added to form a vehicle control group in order to measure background. The plates were incubated at 37° C. for 3 days. A stock solution of $^3$H-thymidine (1 mCi/mL, New England Nuclear, Boston, Mass.) was diluted to 20 µCi/mL in RPMI medium then 20 µL of this solution was added to each well. The plates were further incubated at 37° C. for 8 hours then harvested and analyzed for $^3$H-thymidine uptake using a liquid scintillation counter.

Selected compounds of this invention that inhibit ERK in the colon cell proliferation assay, with an IC$_{50}$ of less than 10 µM include: II-A-43, II-A-48, and II-A-45.

Example 8

The following example demonstrates a process for designing an ERK inhibitor of this invention:

Step 1) Choose a moiety containing a hydrogen bond acceptor as from Table 1, here pick pyrazole (Table 1 structure a).

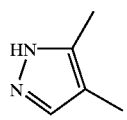

This is Grp2.

Step 2) Confirm that the hydrogen bond acceptor from Grp2 is capable of forming a satisfactory hydrogen bond with the backbone amino hydrogen of Met-108 of ERK.

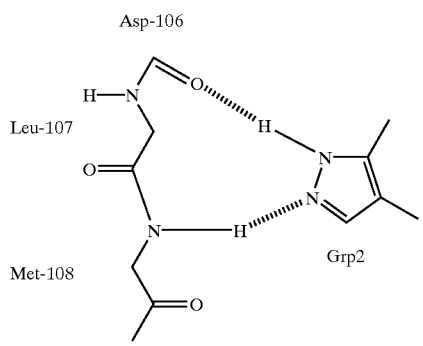

In this case there is an HBD2 group that can also interact favorably with the backbone carbonyl of Asp-106. Step 3) Choose a moiety containing a hydrogen bond donor as from Table 2, here choose pyrrole (Table 2 structure aa)

This is Grp3.

Step 4) Confirm that the hydrogen bond donor from Grp3 is capable of forming a satisfactory hydrogen bond with the sidechain carbonyl of Gln-105.

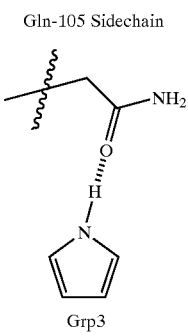

Step 5) Choose a moiety capable of satisfying the distance constraints given for the relative positioning of Grp1 relative to Grp2 and Grp3 while providing substantial attractive interactions with the enzyme environment, here pick benzene.

This is Grp1.

Step 6) Select a connectivity scheme for linking together moieties Grp1, Grp2, and Grp3 from structure types A, B, or C, as described hereinabove.

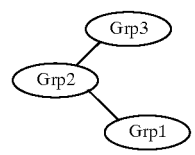

Here we choose structure type A.

Step 7) Provide chemical links corresponding to the structure type selected in Step 6. These links preferably contain the minimum number of bonds consistent with a chemically reasonable structure. Here we pick a valence bond to connect Grp1 to Grp2, and a valence bond to connect Grp 2 to Grp3.

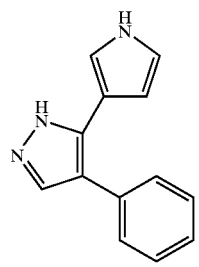

Step 8) Minimize the entire constructed molecule in the context of the active site in order to provide additional R-groups that may be capable of providing further binding to the enzyme (e.g. satisfying unpaired hydrogen bond donors or acceptors or satisfying hydrophobic interactions). Here we connect a —C(=O)NH—CH$_2$—Ph to the 2-position of the pyrrole ring in order to provide a hydrogen bond acceptor (C=O) for the sidechain NH$_3$ of Lys-52 and a hydrophobic group (Ph) for the C(alpha) through C(delta) of Lys-52 and surrounding hydrophobic groups, resulting in compound II-A-5 below.

II-A-5

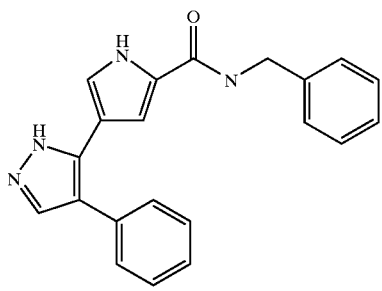

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A composition comprising a compound in an amount sufficient to detectably inhibit ERK protein kinase activity, and a pharmaceutically acceptable carrier, wherein said compound comprises Grp1, Grp2 and Grp3, wherein;

Grp 1 is an optionally substituted phenyl ring;

Grp 2 is selected from

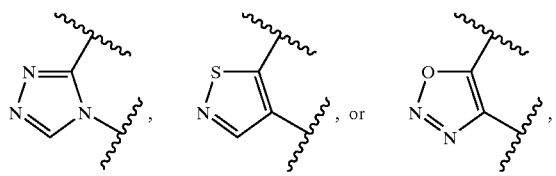

wherein Grp2 has a hydrogen bond acceptor HBA2, and wherein HBA2 is optionally bonded to a hydrogen bond donor HBD2; and Grp3 is a 5-membered heteroaromatic ring having 1-4 nitrogens and a hydrogen bond donor HBD1; wherein said compound optionally comprises a hydrogen bond acceptor HBA1; and wherein Grp1 is within about 2.5–10.0 Å of Grp2; Grp2 is within about 4.0–8.0 Å of Grp3; Grp3 is within about 5.0–12.0 Å of Grp1; HBA2 is within about 6.5–11.0 Å of Grp1; HBD1 is within about 6.5–8.5 Å of Grp2; HBD1 is within about 3.5–5.5 Å of HBA1; and HBA1 is within about 6.7–14.0 Å of HBD2.

2. The composition according to claim 1, wherein the compound comprises hydrogen bond acceptor HBA1.

3. The composition according to claim 1, wherein the hydrogen bond acceptor HBA2 is bonded to a hydrogen bond donor HBD2.

4. The composition according to claim 3, wherein:

Grp1 is within about 3.9–8.0 Å of Grp2; is within about 5.5–6.6 Å of Grp3; Grp3 is within about 6.0–10.0 Å of Grp1; HBA2 is within about 65–11.0 Å of Grp1; HBD1 is within about 7.2–8.2 Å of Grp2; HBD1 is within about 3.9–4.9 Å of HBA1; and HBA1 is within about 7.7–11.7 Å or 11.6–13.6 Å of HBD2.

5. The composition according to claim 4, wherein:

Grp1 is within about 5.7–6.8 Å of Grp2; Grp2 is within about 5.5–6.6 Å of Grp3; Grp3 is within about 7.2–8.2 Å of Grp1; HBA2 is within about 6.5–11.0 Å of Grp1; HBD1 is within about 7.2–8.2 Å of Grp2; HBD1 is within about 3.9–4.9 Å of HBA1; and HBA1 is within about 10.2–11.2 Å or 12.1–13.1 Å of HBD2.

6. The composition according to claim 5 wherein Grp2 is a ring selected from:

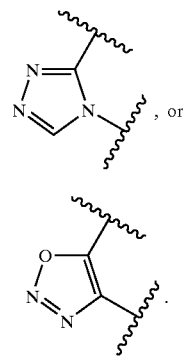

7. The composition according to claim 6 wherein Grp3 is a ring selected from:

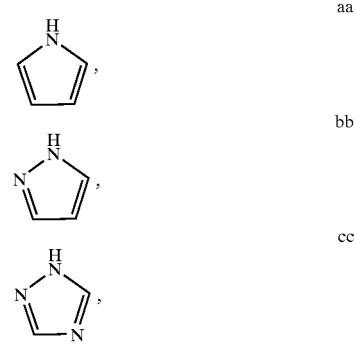

-continued dd 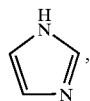

ee 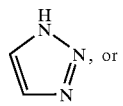

ff 

8. The composition according to claim 7 wherein said compound is formulated in a pharmaceutically acceptable manner for administration to a patient.

9. The composition according to claim 8 further comprising a therapeutic agent, either as part of a multiple dosage form together with said compound or as a separate dosage form.

10. The composition according to claim 1, wherein Grp2 is

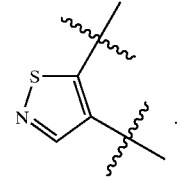

11. The composition according to claim 10, wherein Grp3 is

* * * * *